United States Patent
Legerton et al.

(10) Patent No.: US 11,604,368 B2
(45) Date of Patent: Mar. 14, 2023

(54) CONTACT LENS AND EYEWEAR FRAME DESIGN USING PHYSICAL LANDMARKS PLACED ON THE EYE

(71) Applicant: Innovega, Inc., Bellevue, WA (US)

(72) Inventors: Jerome Legerton, Jupiter, FL (US); Jay Marsh, Bonsall, CA (US)

(73) Assignee: Innovega, Inc., Bellevue, WA (US)

( * ) Notice: Subject to any disclaimer, the term of this patent is extended or adjusted under 35 U.S.C. 154(b) by 165 days.

(21) Appl. No.: 17/223,958

(22) Filed: Apr. 6, 2021

(65) Prior Publication Data

US 2022/0317480 A1    Oct. 6, 2022

(51) Int. Cl.
| | |
|---|---|
| *G02C 13/00* | (2006.01) |
| *A61B 3/14* | (2006.01) |
| *A61B 3/107* | (2006.01) |
| *A61B 3/11* | (2006.01) |
| *A61B 3/00* | (2006.01) |

(52) U.S. Cl.
CPC .......... *G02C 13/003* (2013.01); *A61B 3/0008* (2013.01); *A61B 3/107* (2013.01); *A61B 3/111* (2013.01); *A61B 3/14* (2013.01)

(58) Field of Classification Search
CPC ..... G02C 13/003; A61B 3/0008; A61B 3/107; A61B 3/111; A61B 3/14; A61B 3/0025
USPC ....................................................... 351/219
See application file for complete search history.

(56) References Cited

U.S. PATENT DOCUMENTS

| | | | |
|---|---|---|---|
| 6,003,991 A | 12/1999 | Viirre | |
| 9,304,332 B2 | 4/2016 | Fonte et al. | |
| 9,529,213 B2 | 12/2016 | Fonte et al. | |
| 9,703,123 B2 | 7/2017 | Fonte et al. | |
| 9,880,441 B1 | 1/2018 | Osterhout | |
| 10,031,350 B2 | 7/2018 | Fonte et al. | |
| 10,031,351 B2 | 7/2018 | Fonte et al. | |
| 10,222,635 B2 | 3/2019 | Fonte et al. | |
| 10,330,958 B2 | 6/2019 | Fonte et al. | |
| 10,451,900 B2 | 10/2019 | Fonte et al. | |
| 10,459,256 B2 | 10/2019 | Fonte et al. | |
| 10,495,885 B2 | 12/2019 | Hilkes | |
| 10,536,783 B2 | 1/2020 | Sanger et al. | |
| 10,698,236 B2 | 6/2020 | Fonte et al. | |
| 10,777,018 B2 | 9/2020 | Varady et al. | |
| 2011/0025979 A1 | 2/2011 | Chehab et al. | |
| 2011/0184830 A1 | 7/2011 | Guillox et al. | |
| 2012/0062844 A1 | 3/2012 | Svochak et al. | |
| 2013/0318776 A1 | 12/2013 | Jacobs et al. | |
| 2014/0063055 A1 | 3/2014 | Osterhout | |

(Continued)

OTHER PUBLICATIONS

International Search Report and Written Opinion in PCT/US2021/038737, dated Sep. 30, 2021.

(Continued)

*Primary Examiner* — Mohammed A Hasan

(57) ABSTRACT

A method comprises: disposing a physical landmark upon an eye of a user; capturing at least one image of the eye of the user with an image sensor while the eye is illuminated, wherein the image includes an image of the physical landmark and at least one other point on the surface of the eye outside of the cornea; processing the at least one image to obtain at least one metric of the eye of the user; and determining, based on the at least one metric, at least one parameter of a daily use contact lens to be worn on the eye of the user.

21 Claims, 36 Drawing Sheets

(56) References Cited

U.S. PATENT DOCUMENTS

| | | |
|---|---|---|
| 2014/0118680 A1 | 5/2014 | Chang |
| 2015/0002676 A1 | 1/2015 | Yoo |
| 2016/0282628 A1 | 9/2016 | Hilkes |
| 2017/0068119 A1 | 3/2017 | Antaki |
| 2017/0269385 A1 | 9/2017 | Fonte et al. |
| 2018/0205932 A1 | 7/2018 | Yu et al. |
| 2018/0227470 A1 | 8/2018 | Ronngren |
| 2018/0336737 A1 | 11/2018 | Varady et al. |
| 2019/0179409 A1 | 6/2019 | Jones et al. |
| 2019/0274543 A1 | 9/2019 | Van Der Steen et al. |
| 2020/0285081 A1 | 9/2020 | Fonte et al. |
| 2020/0410775 A1 | 12/2020 | Varady et al. |
| 2021/0369111 A1* | 12/2021 | Dana ................. A61B 3/16 |

OTHER PUBLICATIONS

International Search Report and Written Opinion for Application No. PCT/US2022/022638, dated Jun. 16, 2022, 12 pages.

* cited by examiner

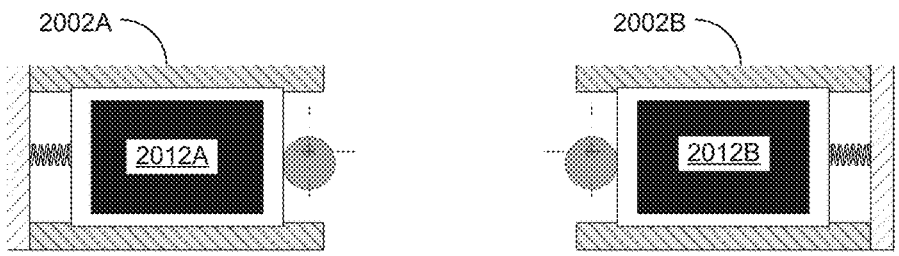
FIG. 20A
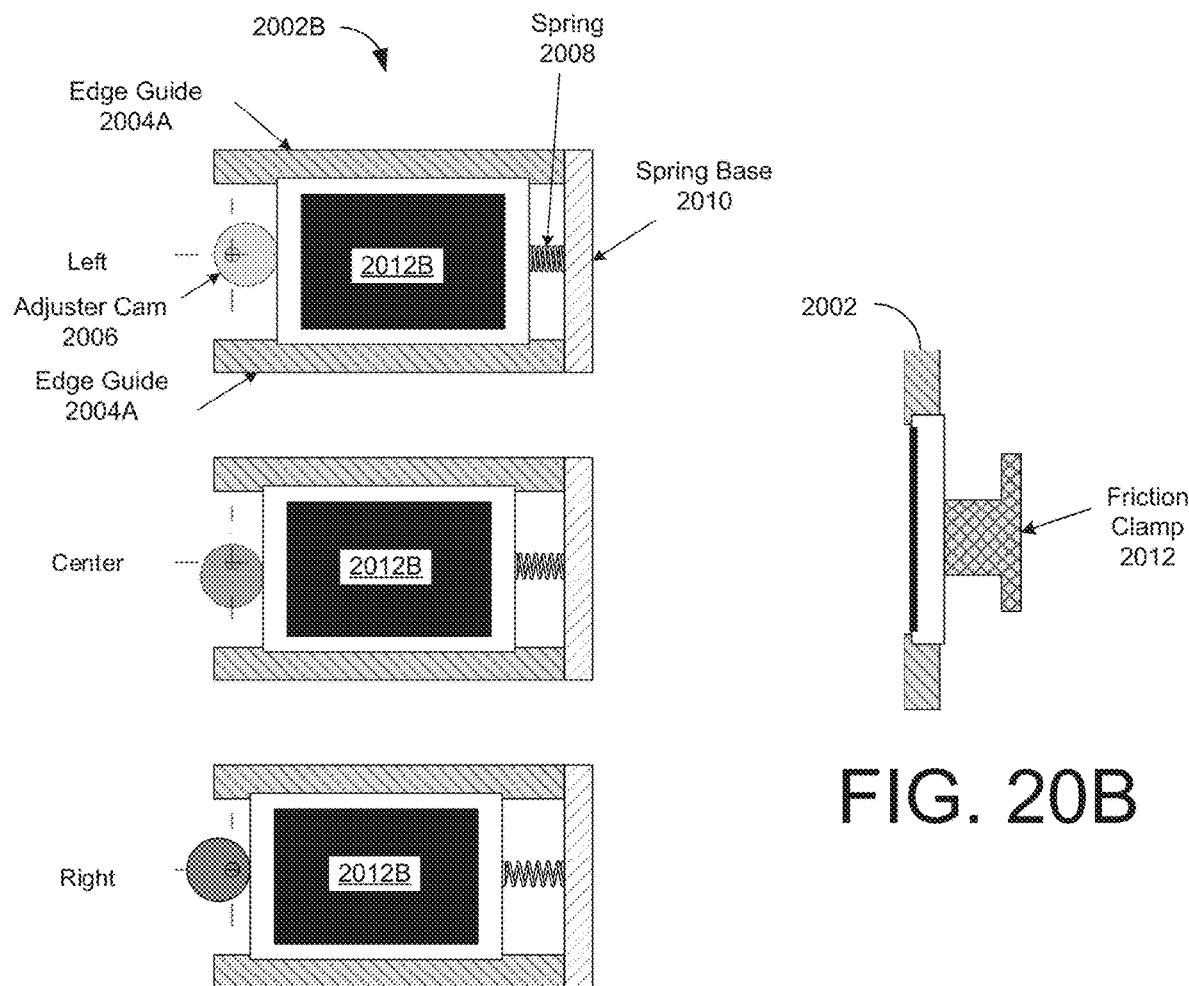
FIG. 20B
FIG. 20C

FIG. 29

Diagonal 0.7 Inch Display 16:9 Aspect
Horizontal Width = 15.5 mm
33% Maximum Pixel Shift

2900

| Pupillary Distance (mm) | Head Width (mm) | | | | | | | | | | | | |
|---|---|---|---|---|---|---|---|---|---|---|---|---|---|
| | 125 | 130 | 135 | 140 | 145 | 150 | 155 | 160 | 165 | 170 | 175 | 180 | 185 |
| 52 | S | S | | | | | | | | | | | |
| 53 | S | S | | | | | | | | | | | |
| 54 | S | S | | | | | | | | | | | |
| 55 | S | S | | | | | | | | | | | |
| 56 | S | S | | | | | | | | | | | |
| 57 | S | S | | S | S | S | S,M | | | | | | |
| 58 | S | S | | S | S | S | S,M | | | | | | |
| 59 | S | S | | S | S,M | S,M | M | M | M | | | | |
| 60 | S | S | | S | S,M | S,M | M | M | M | M | | | |
| 61 | S | S | | S | S,M | S,M | M | M | M | M | | | |
| 62 | S | S | | S,M | S,M | M | M | M | M | M | | | |
| 63 | S | S | S,M | S,M | S,M | M | M | M | M | M | | | |
| 64 | S | S | S,M | M | M | M | M | M | M | M,L | M,L | | |
| 65 | S | S | S,M | M | M | M | M | M | M | M,L | M,L | | |
| 66 | S | | | M | M | M | M | M,L | M,L | M,L | M,L | | |
| 67 | | | | | M | M | M | M,L | M,L | M,L | | | |
| 68 | | | | | | M | M,L | M,L | M,L | M,L | | | |
| 69 | | | | | | | M,L | L | L | L | L | L | L |
| 70 | | | | | | | M,L | L | L | L | L | L | L |
| 71 | | | | | | | | L | L | L | L | L | L |
| 72 | | | | | | | | | L | L | L | L | L |
| 73 | | | | | | | | | L | L | L | L | L |
| 74 | | | | | | | | | L | L | L | L | L |
| 75 | | | | | | | | | L | L | L | L | L |
| 76 | | | | | | | | | L | L | L | L | L |

CONTACT LENS AND EYEWEAR FRAME DESIGN USING PHYSICAL LANDMARKS PLACED ON THE EYE

CROSS REFERENCE TO RELATED APPLICATIONS

The present application is related to U.S. patent application Ser. No. 16/915,985, filed Jun. 29, 2020, entitled "DISPLAY EYEWEAR WITH ADJUSTABLE CAMERA DIRECTION," the disclosure thereof incorporated by reference herein in its entirety.

DESCRIPTION OF RELATED ART

The disclosed technology relates generally to eyewear, and more particularly some embodiments relate to fitting eyewear.

SUMMARY

In general, one aspect disclosed features a method comprising: disposing a physical landmark upon an eye of a user; capturing at least one image of the eye of the user with an image sensor while the eye is illuminated, wherein the image includes an image of the physical landmark and at least one other point on the surface of the eye outside of the cornea; processing the at least one image to obtain at least one metric of the eye of the user; and determining, based on the at least one metric, at least one parameter of a daily use contact lens to be worn on the eye of the user.

Embodiments of the method may include one or more of the following features. In some embodiments, the daily use contact lens is to be worn by the user to view daily use display eyewear. Some embodiments comprise disposing measurement display eyewear on the face of the user prior to capturing the image, the measurement display eyewear comprising a display, the light source, and the image sensor; and capturing the at least one image of the eye of the user and the physical landmark with the display eyewear while the eye is illuminated. In some embodiments, the obtained at least one metric further comprises at least one of: a vertex distance between an apex of a cornea of the eye and the display, a pupillary distance between the center of a pupil of an eye and the midline of the face between the eyes, or a vertical position of the center of the pupil relative to the center of the display. In some embodiments, the physical landmark is a measurement contact lens. In some embodiments, the measurement contact lens comprises an orientation mark; and capturing at least one image of the eye of the user and the physical landmark with an image sensor while the eye is illuminated comprises capturing at least one image of the orientation mark. In some embodiments, the physical landmark comprises a liquid film. In some embodiments, the liquid film reflects light in the spectrum of the image sensor. Some embodiments comprise disposing a measurement contact lens upon the eye of the user prior to capturing the at least one image, wherein the measurement contact lens conforms to the shape of the eye of the user and at least one point on the measurement contact lens is detectable by the image sensor.

In general, one aspect disclosed features non-transitory machine-readable storage medium encoded with instructions executable by one or more hardware processors of a computing component, the machine-readable storage medium comprising instructions to cause the one or more hardware processors to perform operations comprising: receiving at least one image of an eye of a user captured while a physical landmark is on the eye and the eye is illuminated, wherein the image includes an image of the physical landmark and at least one other point on the surface of the eye outside of the cornea; processing the at least one image to obtain at least one metric of the eye of the user; and determining, based on the at least one metric, at least one parameter of a daily use contact lens to be worn on the eye of the user.

Embodiments of the non-transitory machine-readable storage medium may include one or more of the following features. In some embodiments, the daily use contact lens is to be worn by the user to view daily use display eyewear. In some embodiments, the at least one image is captured by measurement display eyewear worn on the face of the user. In some embodiments, the obtained at least one metric further comprises at least one of: a vertex distance between an apex of a cornea of the eye and a display of the measurement display eyewear; a pupillary distance between the center of a pupil of an eye and the midline of the face between the eyes; or a vertical position of the center of the pupil relative to the center of the display. In some embodiments, the physical landmark is a measurement contact lens. In some embodiments, the measurement contact lens comprises an orientation mark; and the at least one image includes an image of the orientation mark. In some embodiments, the measurement contact lens conforms to the surface of the eye; and at least one point on the measurement contact lens is detectable by an image sensor that generated the image. In some embodiments, the physical landmark comprises a liquid film. In some embodiments, the liquid film reflects light in the spectrum of the image sensor that generated the image.

In general, one aspect disclosed features a system, comprising: a hardware processor; and a non-transitory machine-readable storage medium encoded with instructions executable by the hardware processor to perform operations comprising: receiving at least one image of an eye of a user captured while a physical landmark is on the eye and the eye is illuminated, wherein the image includes an image of the physical landmark and at least one other point on the surface of the eye outside of the cornea; processing the at least one image to obtain at least one metric of the eye of the user; and determining, based on the at least one metric, at least one parameter of a daily use contact lens to be worn on the eye of the user.

Embodiments of the system may include one or more of the following features. In some embodiments, the daily use contact lens is to be worn by the user to view daily use display eyewear. In some embodiments, the at least one image is captured by measurement display eyewear worn on the face of the user. In some embodiments, the obtained at least one metric further comprises at least one of: a vertex distance between an apex of a cornea of the eye and a display of the measurement display eyewear; a pupillary distance between the center of a pupil of an eye and the midline of the face between the eyes; or a vertical position of the center of the pupil relative to the center of the display. In some embodiments, the physical landmark is a measurement contact lens. In some embodiments, the measurement contact lens comprises an orientation mark; and the at least one image includes an image of the orientation mark. In some embodiments, the measurement contact lens conforms to the surface of the eye; and at least one point on the measurement contact lens is detectable by an image sensor that generated the image. In some embodiments, the physical landmark comprises a liquid film. In some embodiments, the liquid film reflects light in the spectrum of the image sensor that generated the image.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

FIGS. 20A,B,C illustrate mechanisms for adjusting eyewear displays horizontally according to some embodiments of the disclosed technology.

FIG. 29 is an example data structure for determining parameters of display eyewear for a user based on the user's metrics.

The figures are not exhaustive and do not limit the present disclosure to the precise form disclosed.

DETAILED DESCRIPTION

Embodiments of the disclosure provide systems and methods for fitting eyewear. The eyewear may include eyeglasses, display eyewear, contact lenses to be worn with display eyewear, and contact lenses to be worn without display eyewear. According to the described embodiments, multifunction devices acquire images of the eye. The images are automatically processed to generate design parameters for the eyewear.

Figure 1:
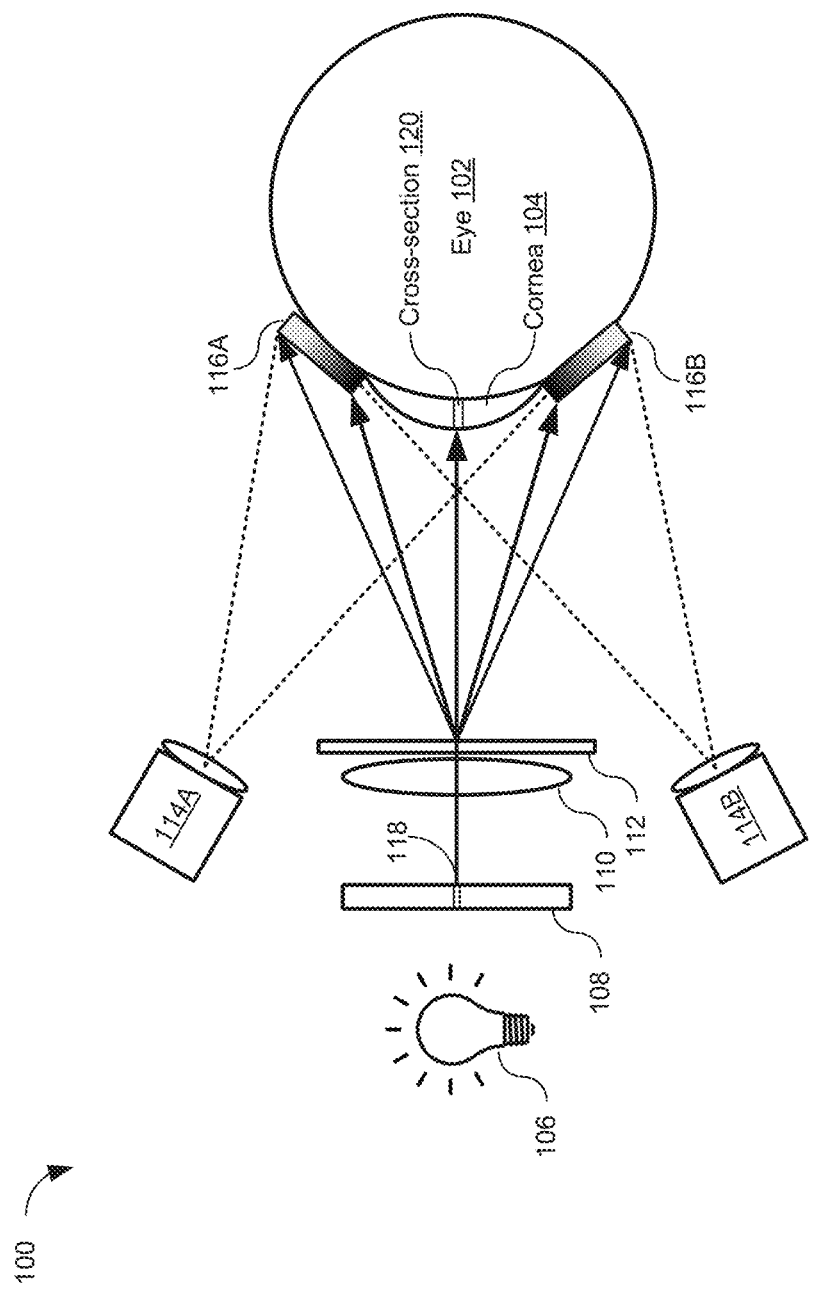
FIG. 1 illustrates an image capture system for capturing images of the eye of a user according to some embodiments of the disclosed technology.

Some embodiments of the disclosure provide systems and methods for automated contact lens design through image capture of the eye. FIG. 1 illustrates an image capture system 100 for capturing images of the eye of a user according to some embodiments of the disclosed technology. Referring to FIG. 1, the eye 102 is shown, as well as the cornea 104 of the eye. The image capture system 100 may include a projection system that includes a light source 106, a panel 108 having an illuminate slit 118 formed therethrough, a lens 110, and a diffraction grating 112. The image capture system 100 may also include one or more cameras 114A,B, which may be positioned on opposite sides of the projection system.

With the light source 106 on, the lens 110 may image the illuminate slit 118 onto the cornea 104, thereby creating a cross-section 120 through the cornea 104, as shown at 120. The diffraction grating 112 may disperse the light into first diffraction orders, thereby projecting light spectra onto the sclera of the eye 102, as depicted at 116A,B. Although FIG. 1 is not a color image, it will be apparent to one skilled in the relevant arts that, within each projected spectrum, the color red will be lateral, while the color violet will be medial. Each camera 114 may capture one or more images of the eye 102 and cornea 104, which may include images of the spectra 116 and the cross-section 120.

Figure 2:
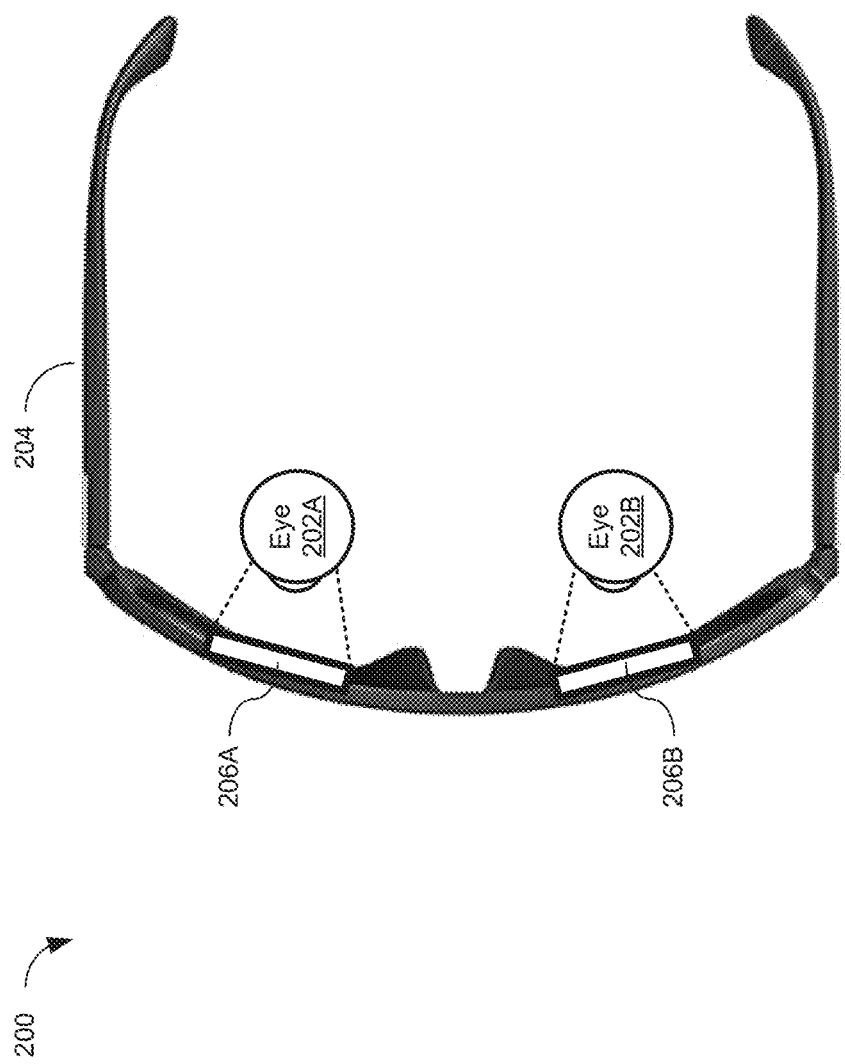
FIG. 2 illustrates an embodiment where the elements of the image capture system of FIG. 1 may be arranged in a pair of spectacles.

The elements of the image capture system 100 of FIG. 1 may be arranged in a variety of multifunction devices. In some embodiments, the elements of the image capture system 100 of FIG. 1 may be arranged in a pair of spectacles. FIG. 2 illustrates one such embodiment. Referring to FIG. 2, a multifunction device 200 includes a pair of spectacles 204 and two image capture systems 206A,B arranged to capture images of the user's eye's 202A,B. In some embodiments, the elements of the image capture system may be in a hand held device or an instrument with a chin and/or a forehead rest. In another embodiment, the elements of the image capture system may employ a mobile phone camera. A control system (not shown) to control the image capture subsystems 206 may be included in the multifunction device 200, may be located externally to the multifunction device 200, or a combination thereof. In embodiments where some or all of the control system is external to the multifunction device 200, the multifunction device 200 may include a receiver or transceiver for connecting the multifunction device 200 to the external elements.

Figure 3:
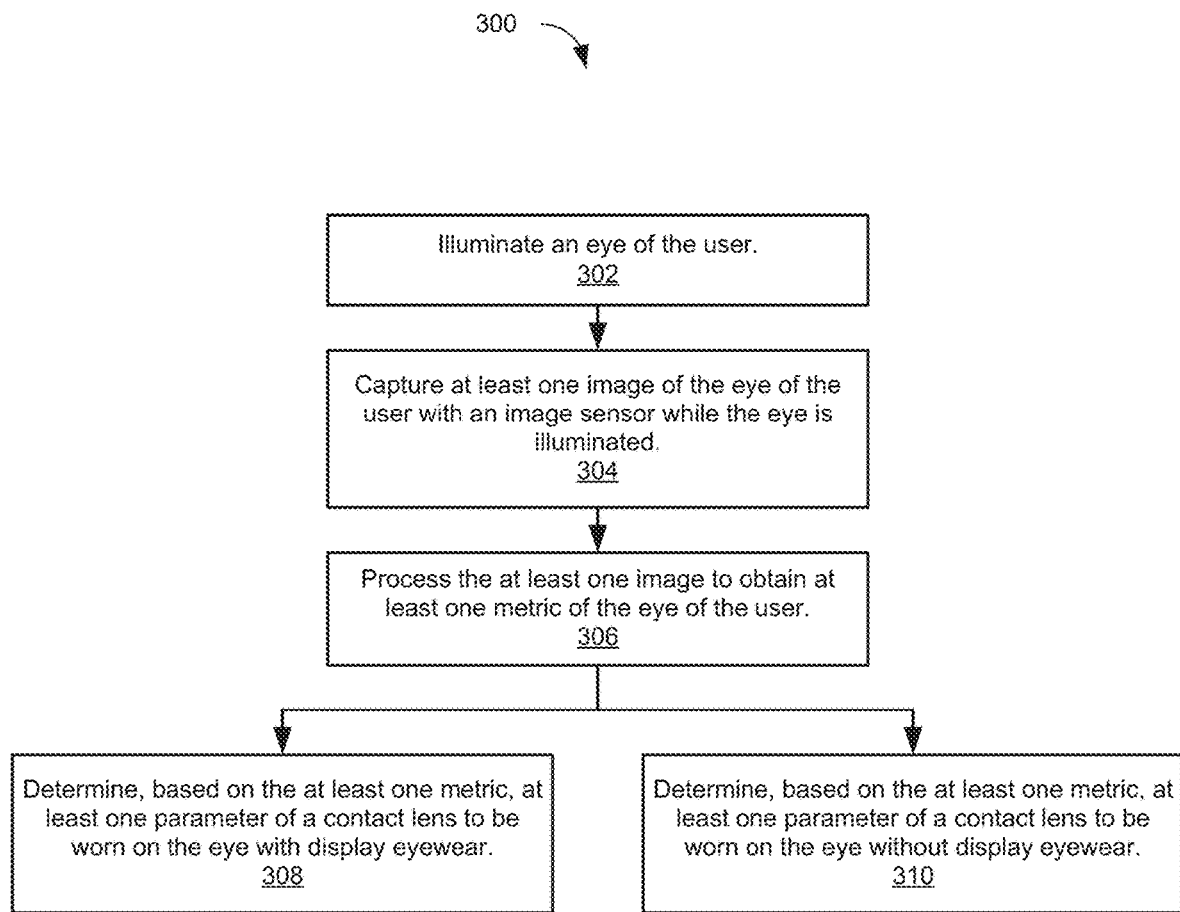
FIG. 3 is a flowchart illustrating a process for automated contact lens design through image capture of the eye according to some embodiments of the disclosed technology.

FIG. 3 is a flowchart illustrating a process 300 for automated contact lens design through image capture of the eye according to some embodiments of the disclosed technology. The elements of the process 300 are presented in one arrangement. However, it should be understood that one or more elements of the process may be performed in a different order, in parallel, omitted entirely, and the like. Furthermore, the process 300 may include other elements in addition to those presented.

Referring to FIG. 3, the process 300 may include illuminating an eye of the user with at least one light source, at 302. For example, referring again to FIG. 1, the eye 102 of the user may be illuminated by the light source 106 of the image capture system 100, via the illuminate slit 118 of the panel 108, the lens 110, and the diffraction grating 112. In other embodiments, ambient light may be used to illuminate the eye, and no other light sources are used.

Referring again to FIG. 3, the process 300 may include capturing at least one image of the eye of the user with an image sensor while the eye is illuminated, at 304. For example, referring again to FIG. 1, each camera 114A,B may capture one or more images of the eye 102 while the eye 102 is illuminated.

Referring again to FIG. 3, the process 300 may include processing the at least one image to obtain at least one metric of the eye of the user, at 306. In some embodiments, this processing may include the use of artificial intelligence techniques. For example, a machine-learning model may be trained using obtained metrics and associated parameters for a large number of users, using supervised and/or unsupervised training techniques. The trained machine-learning model may be provided with a user's metrics as inputs, and may provide the parameters as outputs.

Figure 4:
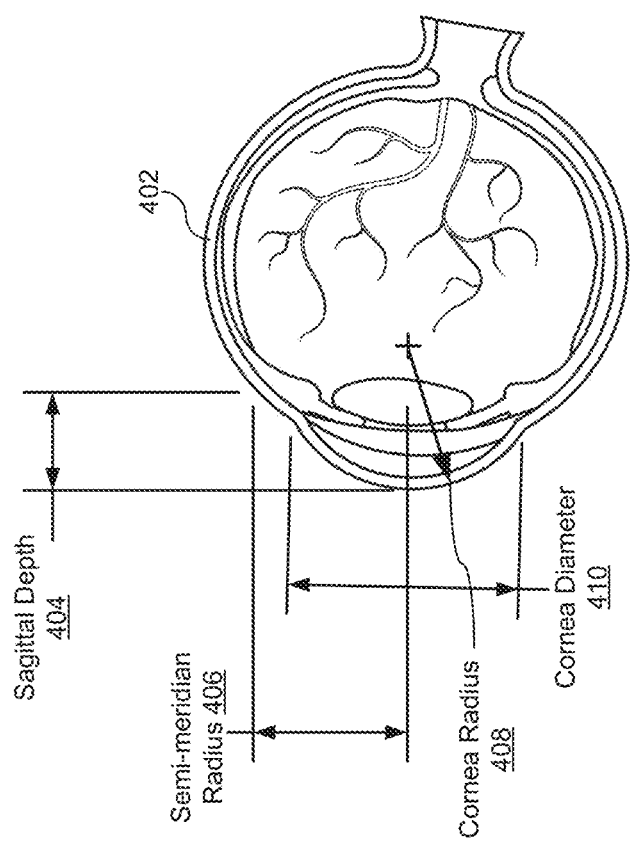
FIG. 4 illustrates metrics of the eye that may be determined by processing the captured images.

FIG. 4 illustrates metrics of the eye 402 that may be determined by processing the captured images. Referring to FIG. 4, the metrics may include a sagittal depth 404 of the eye 402 of the sclera for at least one semi-meridian radial distance outside the cornea. The metrics may include a radius 406 of a semi-meridian of the eye 402. The metrics may include a radius of curvature 408 of the cornea of the eye 402. The metrics may include a diameter 410 of the cornea of the eye 402. The metrics may include a position of a center of the pupil or first Purkinje image of the eye (not shown). The metrics may include a position and an aperture height between the lids of the eye (not shown). Other metrics may be determined as well including the vertex distance from the apex of the cornea to a reference plane and a scleral distance from a reference plane. These metrics may be determined using the known geometry and other characteristics of the image capture system.

In some embodiments, additional metrics may be determined. For example, when the multifunction device takes the form of a pair of spectacles, the metrics may include a vertex distance between an apex of the cornea of the eye and the spectacle plane of the measurement eyewear, the pupillary distance between the centers of the pupils of the eyes or the distance from the midline of the face between the pupils to the center of a single pupil or the centers of each pupil, referred to as a split pupillary distance, and the sagittal depth of the sclera from the apex of the cornea to a point on at least one semi-chord radial distance outside the cornea. Other metrics are contemplated.

In some embodiments, the multifunction device may take the form of display eyewear. In these embodiments, the metrics may include the vertical position of the center of the pupil of each eye relative to the center of the corresponding display of the display eyewear and similar metrics.

In some embodiments, the obtained metrics may include the sagittal depth of the sclera of an eye of the user for at least one semi-meridian radial distance outside the cornea. In these embodiments, a sagittal depth feature may be determined of the first or second contact lens based on this sagittal depth.

Figure 5:
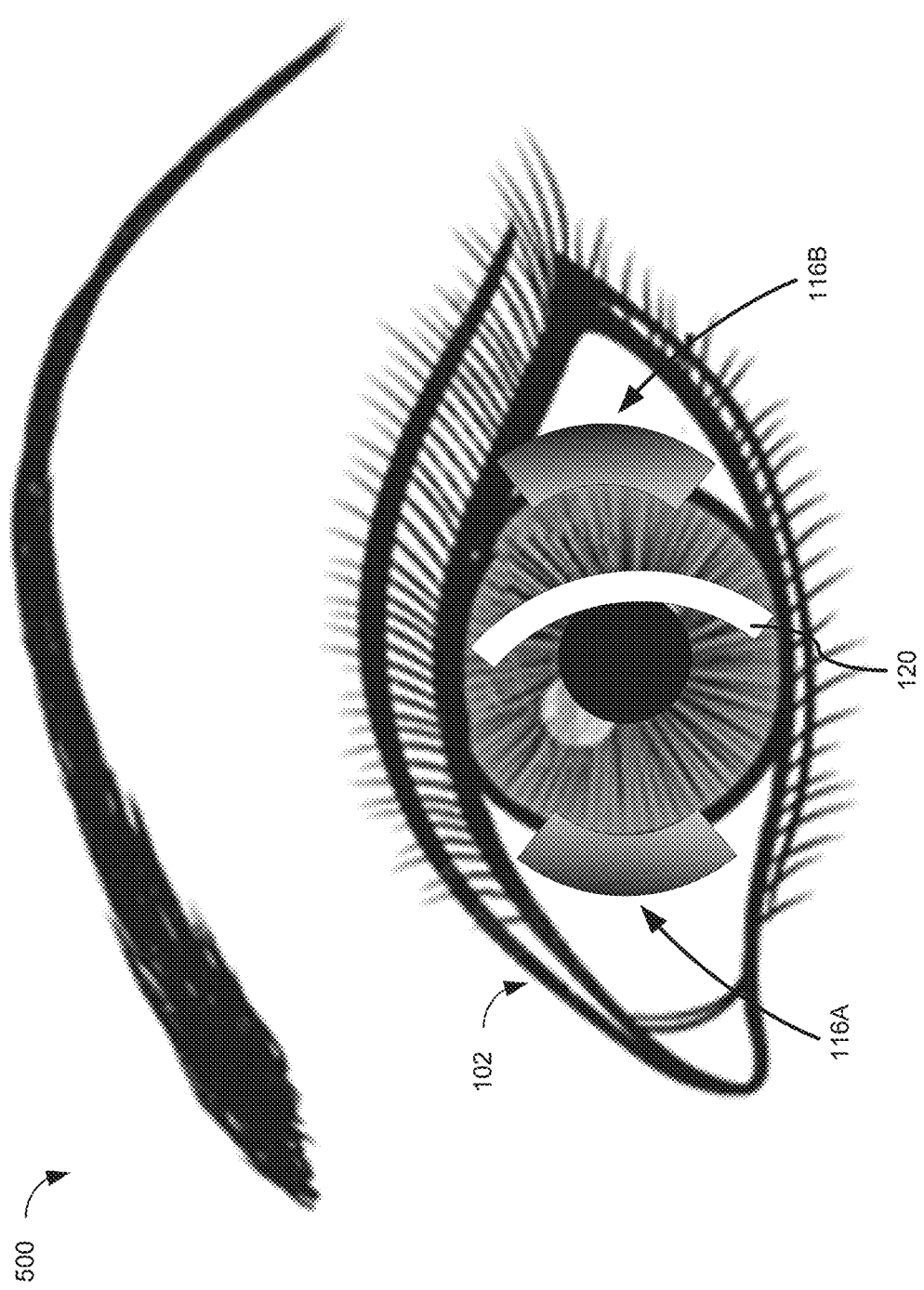
FIG. 5 depicts an example image of the eye captured by the image capture system 100 of FIG. 1.

FIG. 5 depicts an example image 500 of the eye 102 captured by the image capture system 100 of FIG. 1. Referring to FIG. 5, the image includes the cross-section 120, as well as the spectra 116A,B projected on the sclera the eye 102.

Figure 6:
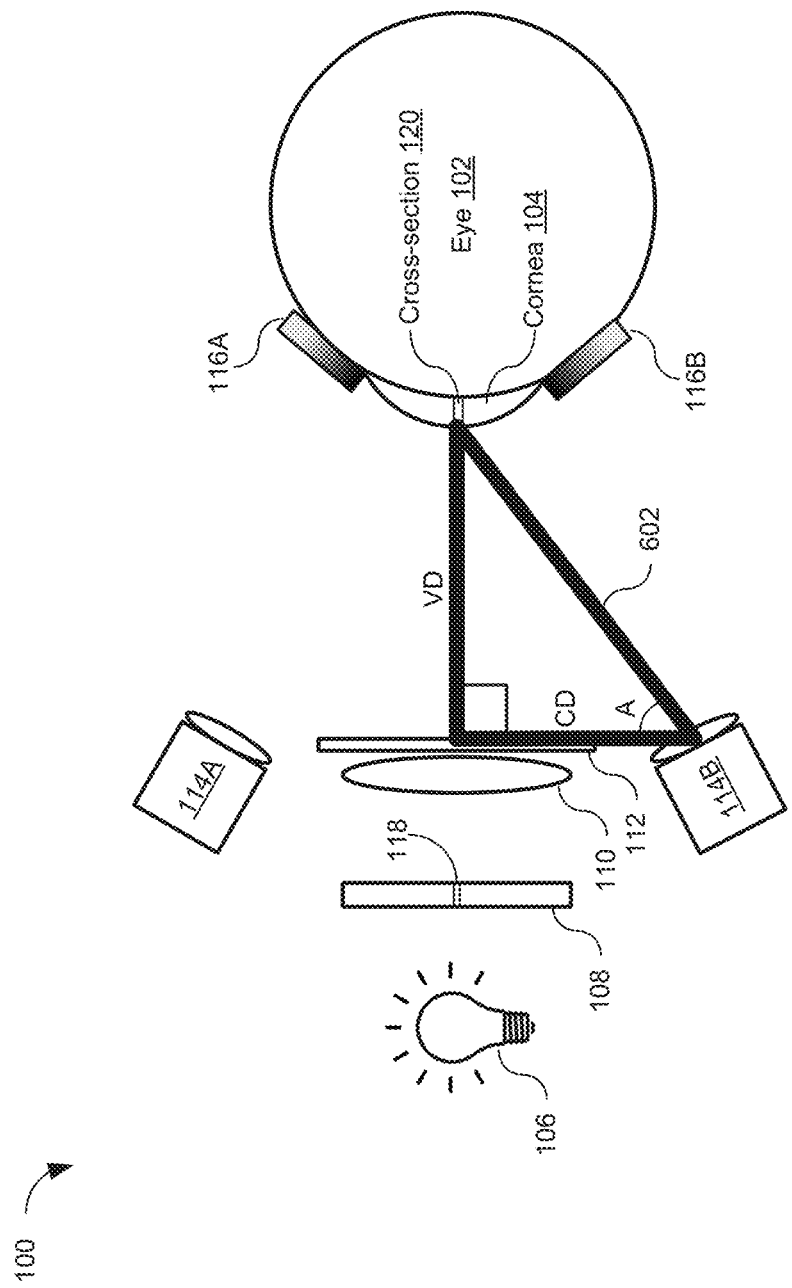
FIG. 6 illustrates an example technique for determining a vertex distance VD, also called an eye-relief distance, for the image capture system of FIG. 1.

FIG. 6 illustrates an example technique for determining a vertex distance VD, also called an eye-relief distance, for the image capture system 100 of FIG. 1. Referring to FIG. 6, the vertex distance VD is the distance between the diffraction grating 112 and the surface of the cornea 104. In the example of FIG. 6, the geometry of the image capture system forms a right triangle 602 from which the vertex distance VD can be determined. In other embodiments, the geometry may form other types of triangles from which the vertex distance VD can be determined.

In the right triangle 602, the distance CD between an opening in the diffraction grating 112 and the center of the lens of the camera 114B is known from manufacturing parameters of the image capture system. The angle A is known from the position of the cross-section 120 in the image captured by the camera 114B, for example as shown in FIG. 5. In this example, the vertex distance VD may be calculated based on the values of the distance CD and the angle A. This process may be employed for images captured by the other camera 114A as well. The vertex distances VD determined according to the images captured by the cameras 114A,B may be averaged, compared, or processed in some other manner to obtain a single vertex distance VD.

Figure 7:
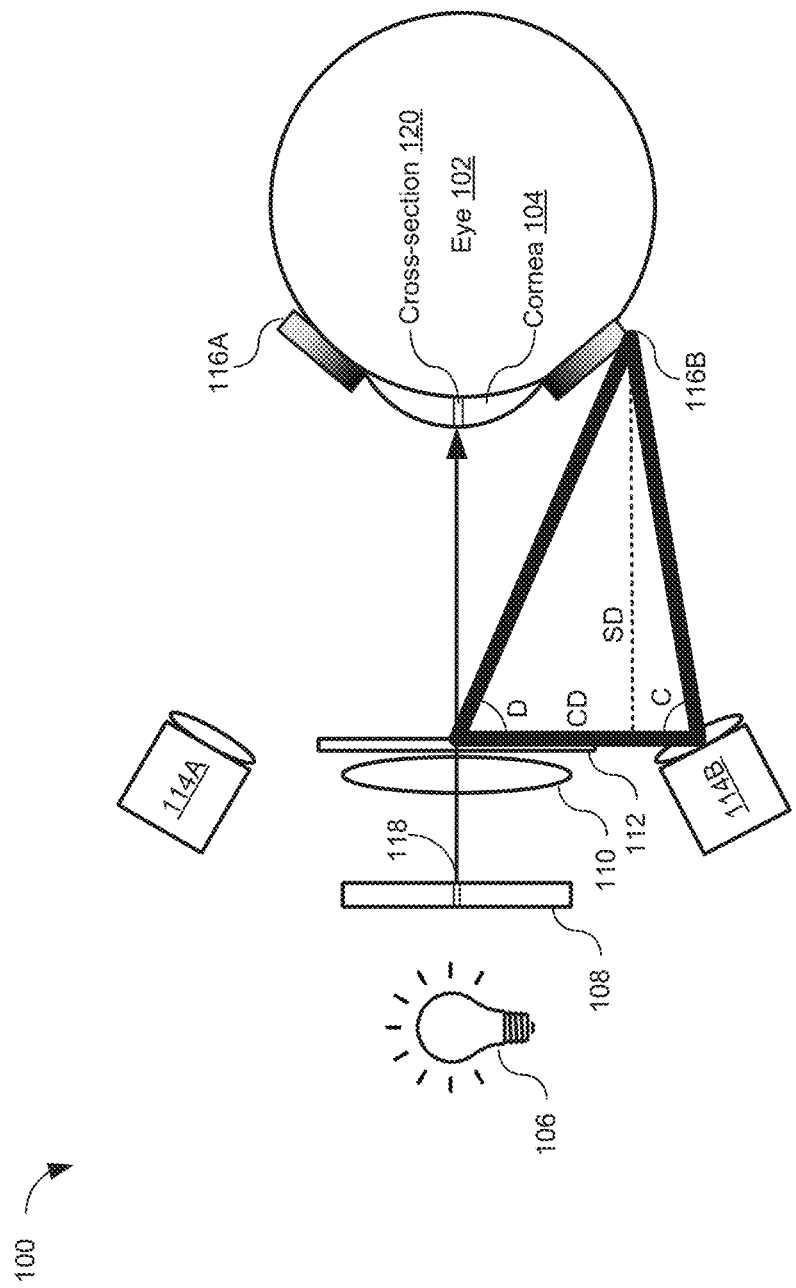
FIG. 7 illustrates an example technique for determining a scleral distance SD for the image capture system of FIG. 1.

FIG. 7 illustrates an example technique for determining a scleral distance SD for the image capture system 100 of FIG. 1. Referring to FIG. 7, the scleral distance SD is the normal distance from the plane of the diffraction grating 112 to the sclera of the eye 102. In the example of FIG. 7, the geometry and characteristics of the image capture system forms a triangle 702 from which the scleral distance SD can be determined.

In the triangle 702, the distance CD between an opening in the diffraction grating 112 and the center of the lens of the camera 114B is known from manufacturing parameters of the image capture system. The angle C is known from the position of the color red in the image of the spectrum 116B captured by the camera 114B. The angle D is known from the dispersion properties of the diffraction grating 112. In this example, the scleral distance SD may be calculated based on the values of the distance CD and the angles C,D. This process may be employed for images captured by the other camera 114A as well. The scleral distances SD determined according to the images captured by the cameras 114A,B may be averaged, compared, or processed in some other manner to obtain a single scleral distance SD. The sagittal depth of the eye at a semi chord outside of the cornea may be calculated by subtracting the distance CD from a respective single scleral distance SD.

Figure 8:
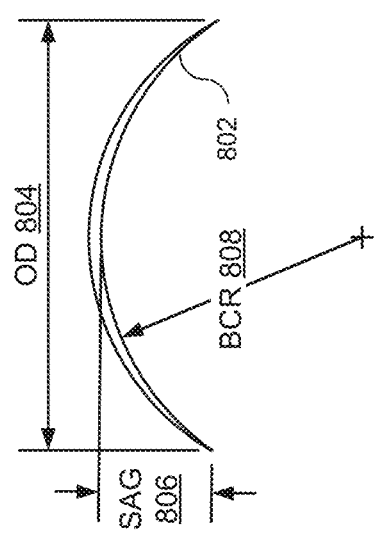
FIG. 8 illustrates various parameters of contact lenses that may be determined according to embodiments disclosed technologies.

Referring again to FIG. 3, the process 300 may include determining, based on the at least one metric, at least one parameter of a contact lens to be worn on the eye with display eyewear, at 308, or at least one parameter of a contact lens to be worn on the eye without display eyewear, at 310. Contact lenses may then be manufactured based on the parameters. FIG. 8 illustrates various parameters of contact lenses that may be determined according to embodiments disclosed technologies. A cross-section of a contact lens 802 is depicted. Also depicted are parameters of the contact lens 802 that include an outer diameter (OD) 804, sagittal depth (SAG) 806, and a base curve radius (BCR) 808. The base curve radius 808 of the contact lens 802 may be determined based on the radius of the cornea the eye. For example, in some embodiments the base curve radius may be equal to the radius of the cornea while in other embodiments the base curve radius may be up to 1.0 mm longer than the radius of the cornea; and in other embodiments the base curve radius may be shorter than the radius of the cornea. The outer diameter 804 of the contact lens 802 may be determined based on the diameter of the cornea of the eye. For example, in some embodiments for corneal contact lenses the outer diameter of the contact lens may be 90% of the diameter of the cornea while in other embodiments for soft contact lenses or scleral contact lenses the outer diameter may be 110% to 150% of the diameter of the cornea respectively. The sagittal depth of the contact lens 802 may be determined based on one or more sagittal depths of the eye. For example, in some embodiments the preferred sagittal depth of a soft lens or rigid scleral lens may be 200 microns or 400 microns, respectively, greater than the sagittal depth of the eye at the same chord diameter.

In some embodiments, the contact lens may include a central optical feature. The central optical feature may be designed to function with display eyewear. In these embodiments, the location of the center optical feature of the contact lens may be determined based on the center of the pupil or the measured location of the first Purkinje image of the eye.

In some embodiments, the determined metrics of the eye may include a position of the lids of an eye and the aperture height between lids of the eye. In these embodiments, a nonrotation feature of the contact lens may be determined based on the position of the eyelids and aperture height between the lids of the eye. Non-rotating features may include double slab-off designs where the superior and inferior aspects of the lens are made thinner than the nasal and temporal aspects of the lens; prism ballast designs where the inferior portion of the lens is made thicker than the superior portion of the lens; non-symmetrical thin and thick zones where the superior aspect of the lens is thinner and inferior nasal and inferior temporal zones are made thicker; or other asymmetric geometries having orientational stability effects. In some embodiments these features may be modulated in position or thickness based on the measured position of the lids and/or the aperture height between the lids through the captured images.

Figure 9:
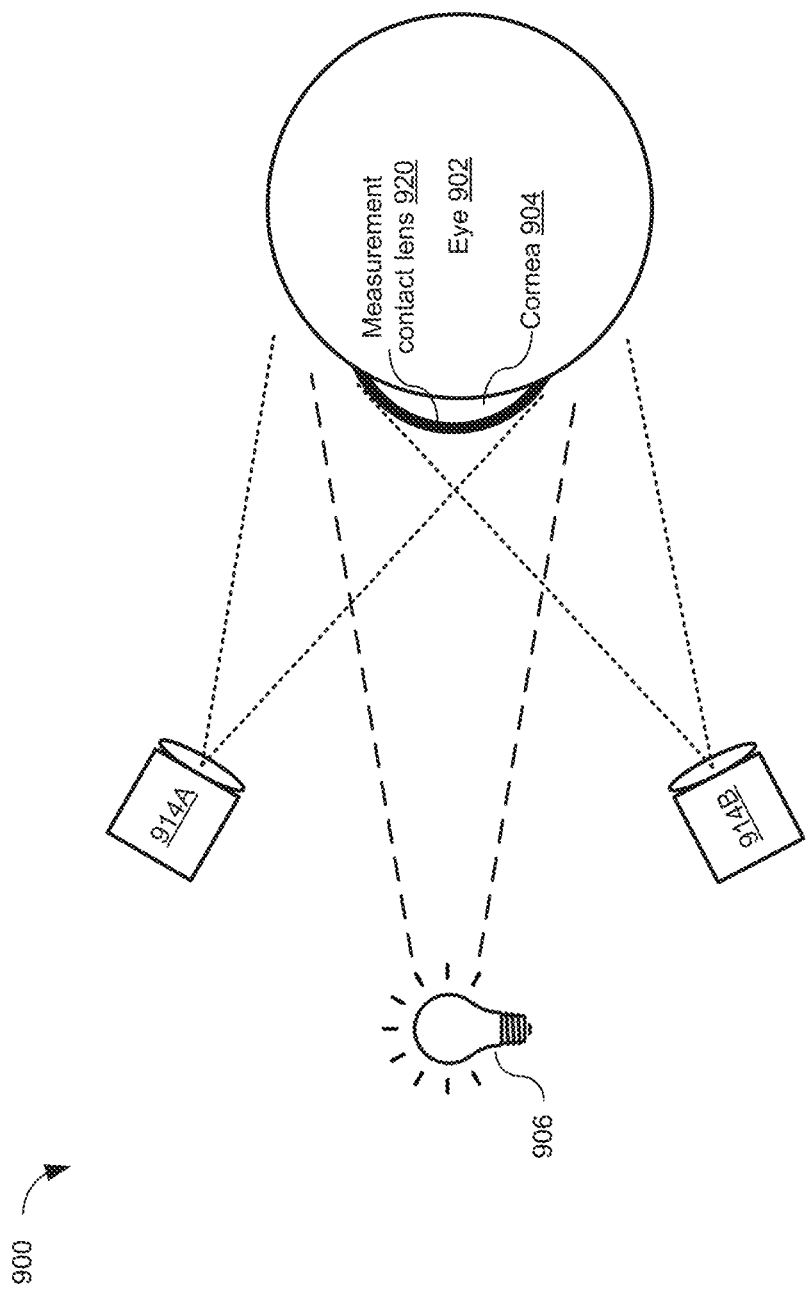
FIG. 9 illustrates an image capture system for capturing images of the eye of a user while wearing a measurement contact lens according to some embodiments of the disclosed technology.

Some embodiments of the disclosure provide systems and methods for automated contact lens design through image capture of an eye wearing a reference contact lens. FIG. 9 illustrates an image capture system 900 for capturing images of the eye of a user while wearing a measurement contact lens according to some embodiments of the disclosed technology. Referring to FIG. 9, the eye 902 is shown, as well as the cornea 904 of the eye. Also shown is a measurement contact lens 920, worn upon the eye 902. The measurement contact lens 920 may be translucent. The image capture system 900 may include a light source 906 and one or more cameras 914A,B, which may be positioned on opposite sides of the light source 906 or by way of a beam combiner aligned with the z axis of the light source. With the light source 906 on and illuminating the eye 902, each camera 914 may capture one or more images of the eye 902 and the measurement contact lens 920. In some embodiments the light source may be aligned with the central axis of the camera.

Figure 10:
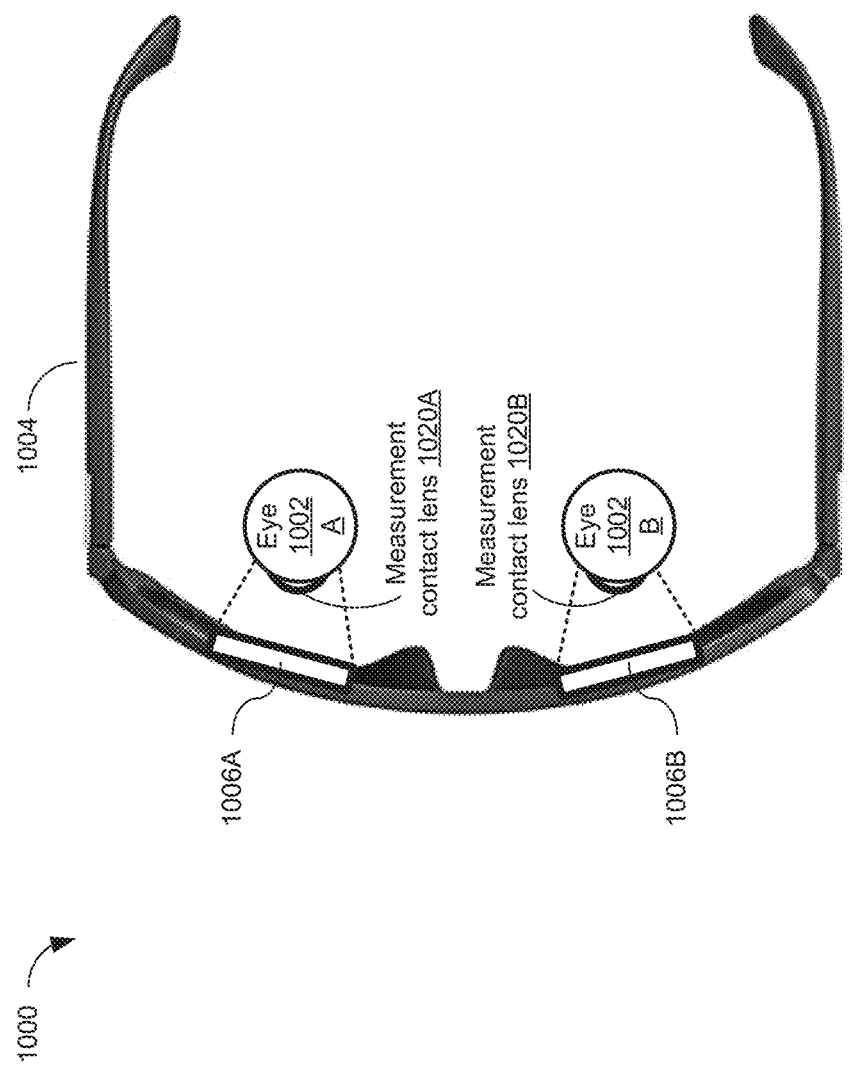
FIG. 10 illustrates an embodiment where the elements of the image capture system of FIG. 9 may be arranged in measurement eyewear.

The elements of the image capture system 900 of FIG. 9 may be arranged in a variety of multifunction devices. In some embodiments, the elements of the image capture system 900 of FIG. 9 may be arranged in measurement eyewear, for example such as a pair of spectacles. FIG. 10 illustrates one such embodiment. Referring to FIG. 10, a multifunction device 1000 includes a pair of spectacles 1004 and two image capture systems 1006A,B arranged to capture images of the user's eyes 1002A,B while wearing measurement contact lenses 1020A,B, respectively. In these embodiments, the measurement eyewear is disposed on the face of the user prior to capturing the images.

A control system (not shown) to control the image capture subsystems 1006 may be included in the multifunction device 1000, may be located externally to the multifunction device 1000, or a combination thereof. In embodiments where some or all of the control system is external to the multifunction device 1000, the multifunction device 1000 may include a receiver or transceiver for connecting the multifunction device 1000 to the external elements.

Figure 11:
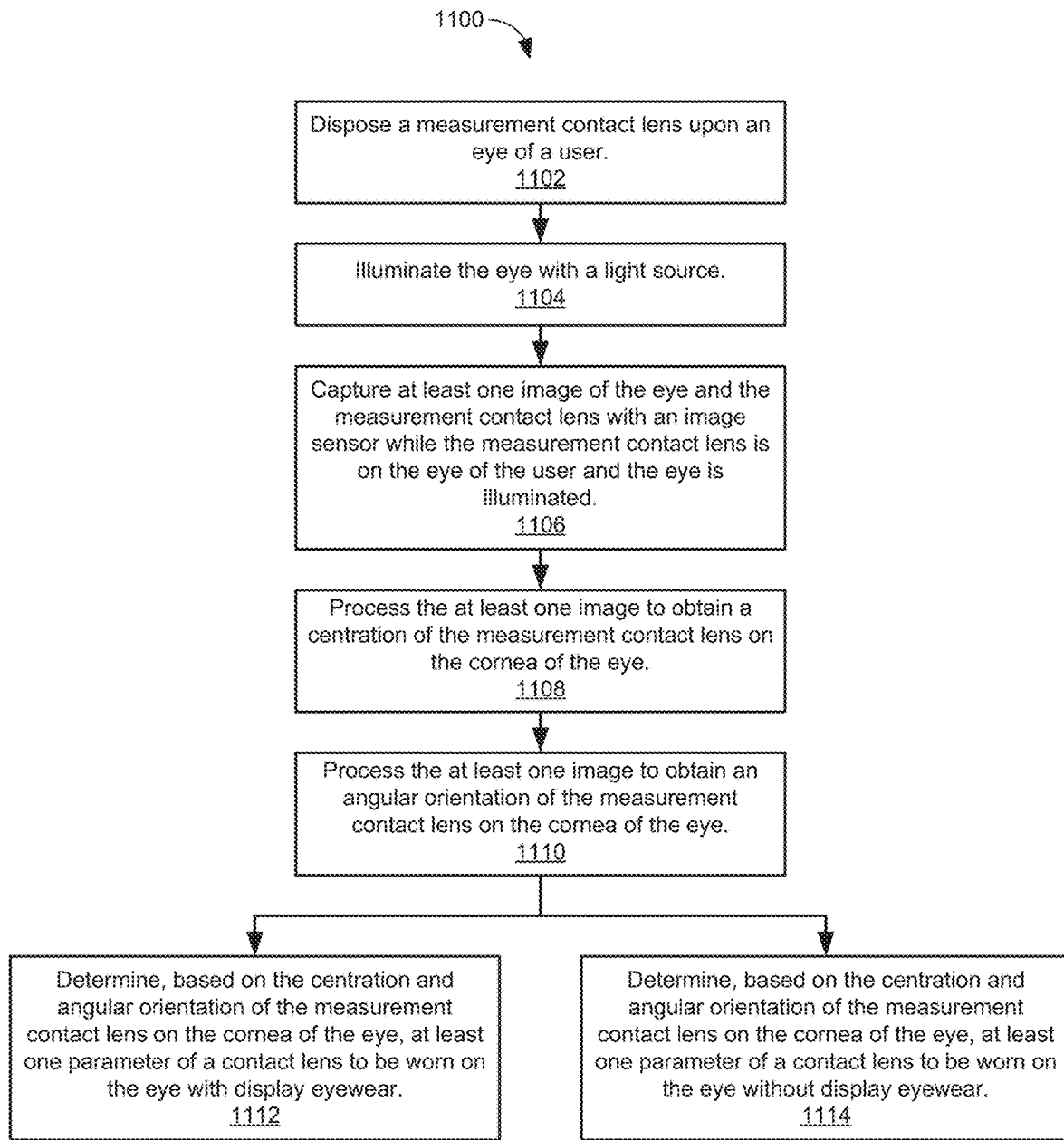
FIG. 11 is a flowchart illustrating a process for automated contact lens design through image capture of the eye wearing a reference contact lens according to some embodiments of the disclosed technology.

FIG. 11 is a flowchart illustrating a process 1100 for automated contact lens design through image capture of the eye wearing a reference contact lens according to some embodiments of the disclosed technology. The elements of the process 1100 are presented in one arrangement. However, it should be understood that one or more elements of the process may be performed in a different order, in parallel, omitted entirely, and the like. Furthermore, the process 1100 may include other elements in addition to those presented.

Referring to FIG. 11, the process 1100 may include disposing a measurement contact lens upon an eye of a user, at 1102. In some embodiments, the measurement contact lens includes orientation marks, patterns, or similar features. In other embodiments, the measurement contact lens has no orientation marks, patterns, or similar features, and is detectable by the camera 114 or image sensor.

Figure 12A:
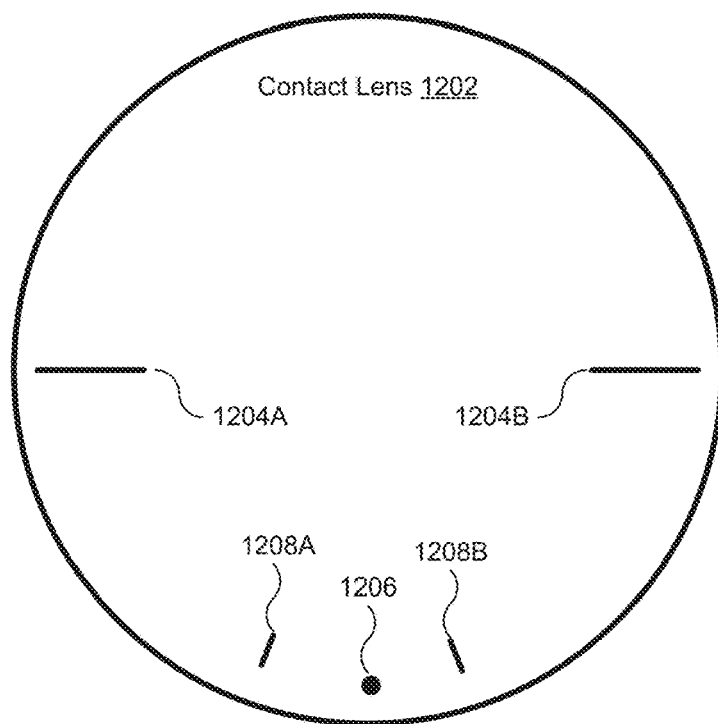
FIG. 12A illustrates an example contact lens having orientation marks according to embodiments of the disclosed technologies.

FIG. 12A illustrates an example contact lens 1202 having orientation marks according to embodiments of the disclosed technologies. Referring to FIG. 12A, the contact lens 1202 may include one or more radial scribe marks. For example, the contact lens 1202 may include a pair of radial scribe marks located near the edge of the contact lens 1202 at the 3 o'clock and 9 o'clock positions, as shown at 1204A and 1204B. As another example, a contact lens 1202 may include a dot 1206 or radial scribe mark at the 6 o'clock position flanked by a pair of radial scribe marks 1208A,B each separated from the dot 1206 by a predetermined angle. In some examples, the angle may be 15 degrees. In other embodiments, these orientation marks may be employed alone or in various combinations with each other, and with other orientation marks. Other orientation marks may include, by way of nonlimiting example portions of a circle, segmented arcs, or three points that are a common distance from the center of the lens. Orientation marks may be cast into the lens substrate, dyes, or inks and may have special properties with regard to detection by spectral image sensors. For example, titanium dioxide may be used to enhance detection with infra-red light sources and infra-red sensors. Orientation marks may be molded into or onto a surface or added by means of removing lens polymer material. Orientation marks may be applied after the lens is made by laser marking, jet printing, transfer printing, or pad printing.

Figure 12B:
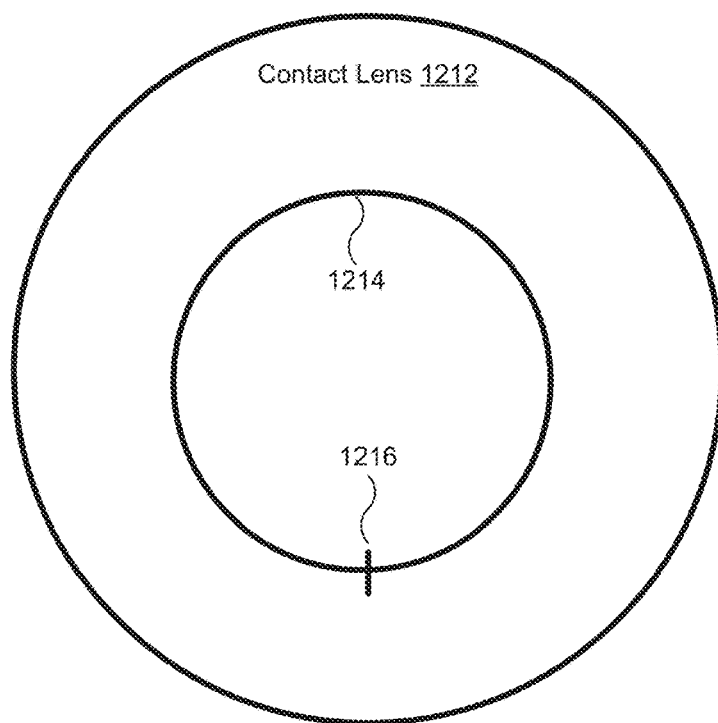
FIG. 12B illustrates another example contact lens having orientation marks according to embodiments of the disclosed technologies.

FIG. 12B illustrates another example contact lens 1212 having orientation marks according to embodiments of the disclosed technologies. Referring to FIG. 12B, the contact lens includes two orientation marks. One orientation mark is a concentric circle 1214. The other orientation mark is a radial scribe mark 1216 intersecting the circle 1214.

Referring again to FIG. 11, the process 1100 may include illuminating the eye with a light source, at 1104, and capturing at least one image of the eye and the measurement contact lens with an image sensor while the measurement contact lens is on the eye of the user and the eye is illuminated, at 1106. For example, referring again to FIG. 9, the eye 902 of the user may be illuminated by the light source 906 of the image capture system 900, and each camera 914A,B may capture one or more images of the eye 902 while the eye 902 is illuminated and the measurement contact lens 920 is on the eye 902. In other embodiments, ambient light may be used to illuminate the eye, and no other light sources are used.

Figure 13:
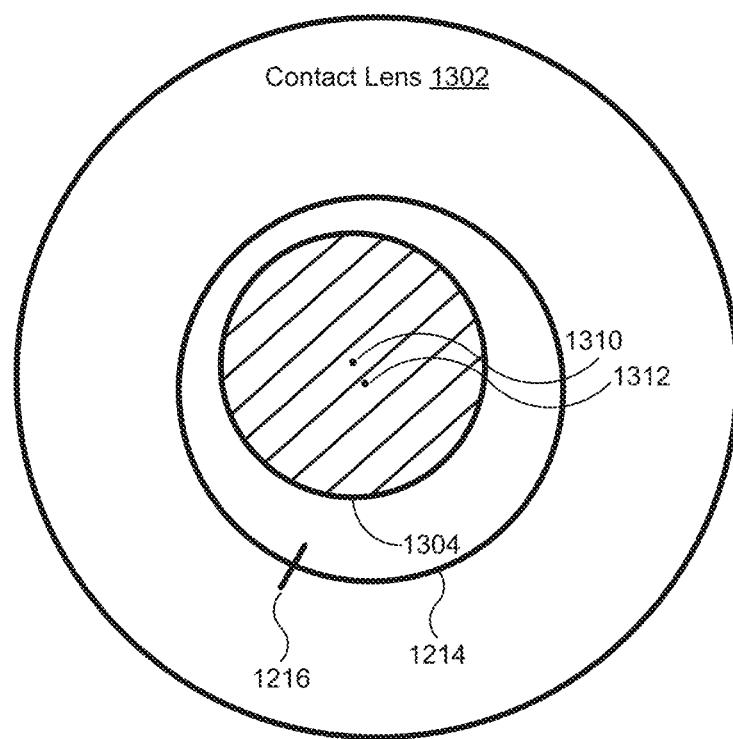
FIG. 13 shows the features of the measurement contact lens, as well as the pupil 1204 of the eye.

In embodiments where the measurement contact lens includes orientation marks, the captured images may include images of the orientation marks. The images may include features of the eye such as the pupil, the visible iris, and the eyelids. FIG. 13 illustrates an example captured image of an eye wearing the example measurement contact lens 1212 of FIG. 12B. FIG. 13 shows the features of the measurement contact lens 1212, as well as the pupil 1204 of the eye.

Referring again to FIG. 11, the process 1100 may include processing the at least one image to obtain a centration of the measurement contact lens on the cornea of the eye, at 1108. For example, referring again to FIG. 13, the center of the measurement contact lens 1212 is shown at 1312, and the center of the pupil is shown at 1310. In some embodiments, the center 1312 of the contact lens 1212 may be determined based on points falling on the outer edge of the measurement contact lens or on points on the orientation mark 1212 or the circle 1214, and the center of the pupil 1304 may be determined based on points falling on the edge of the pupil 1304. The edges of the contact lens and pupil may be determined by an edge detection process or a similar technique. In some embodiments, three points are determined for each edge, and on each edge. In one embodiment, no two points are separated by less than 60 degrees. The center of the contact lens and the center of the pupil may be determined by use of each set of three points on the respective edges. In some embodiments, this processing may include the use of artificial intelligence techniques, for example as described above.

Referring again to FIG. 11, the process 1100 may include processing the at least one image to obtain an angular orientation of the measurement contact lens on the cornea of the eye, at 1110. For example, the angular orientation of the measurement contact lens may be determined by determining an angular displacement of an orientation mark from its original position. In the example of FIG. 13, the angular orientation of the measurement contact lens 1212 may be determined by determining the angular displacement of the orientation mark 1216 from an angular reference orientation.

Referring again to FIG. 11, the process 1100 may include determining, based on the centration and angular orientation of the measurement contact lens on the cornea of the eye, at least one parameter of a contact lens to be worn on the eye with display eyewear, at 1112, or at least one parameter of a contact lens to be worn on the eye without display eyewear, at 1114. Contact lenses may then be manufactured or selected from a collection of contact lenses based on the parameters. For example, the parameters may include those depicted in, and discussed with reference to, FIG. 8. In some embodiments, the parameters may describe a displacement of optics in the contact lens to correct for the lack of centration. These optics may include apertures, filters, lenslets, higher order aberration features, multifocal optics and similar optics. In some embodiments, the parameters may describe a modulation of one or more non-rotating features of the contact lens to correct for the lack of centration.

In some embodiments, this process may include determining an angular orientation and/or vertical position of non-rotational features of the contact lens based on the angular orientation of the measurement contact lens on the cornea of the eye, a position of the lid, and an aperture height between the eyelids. In some embodiments, this process may include determining an angular position of a light polarizing filter and/or micro-lens of the contact lens relative to a non-rotation design feature in the contact lens based on the angular orientation of the measurement contact lens on the cornea of the eye.

In some embodiments, the measured angular orientation of the contact lens may be used to preset the angular orientation of the display light polarization produced by the displays in display eyewear to align with a contact lens containing at least one light polarizing filter. The polarization alignment enhances the display performance by maximizing the transmission and extinction of display light through display and distance optical portions of the lens when linear polarization analyzers are included in the lens. In some embodiments, the polarization of the display light is adjusted with a waveplate optical element that twists the exit polarization angle by twice the angle of the input polarization difference between the incident light and the axis of the waveplate. In other embodiments, an active liquid crystal optical element can be used to twist the polarization angle of the incident polarized light using electronic controls.

Figure 14:
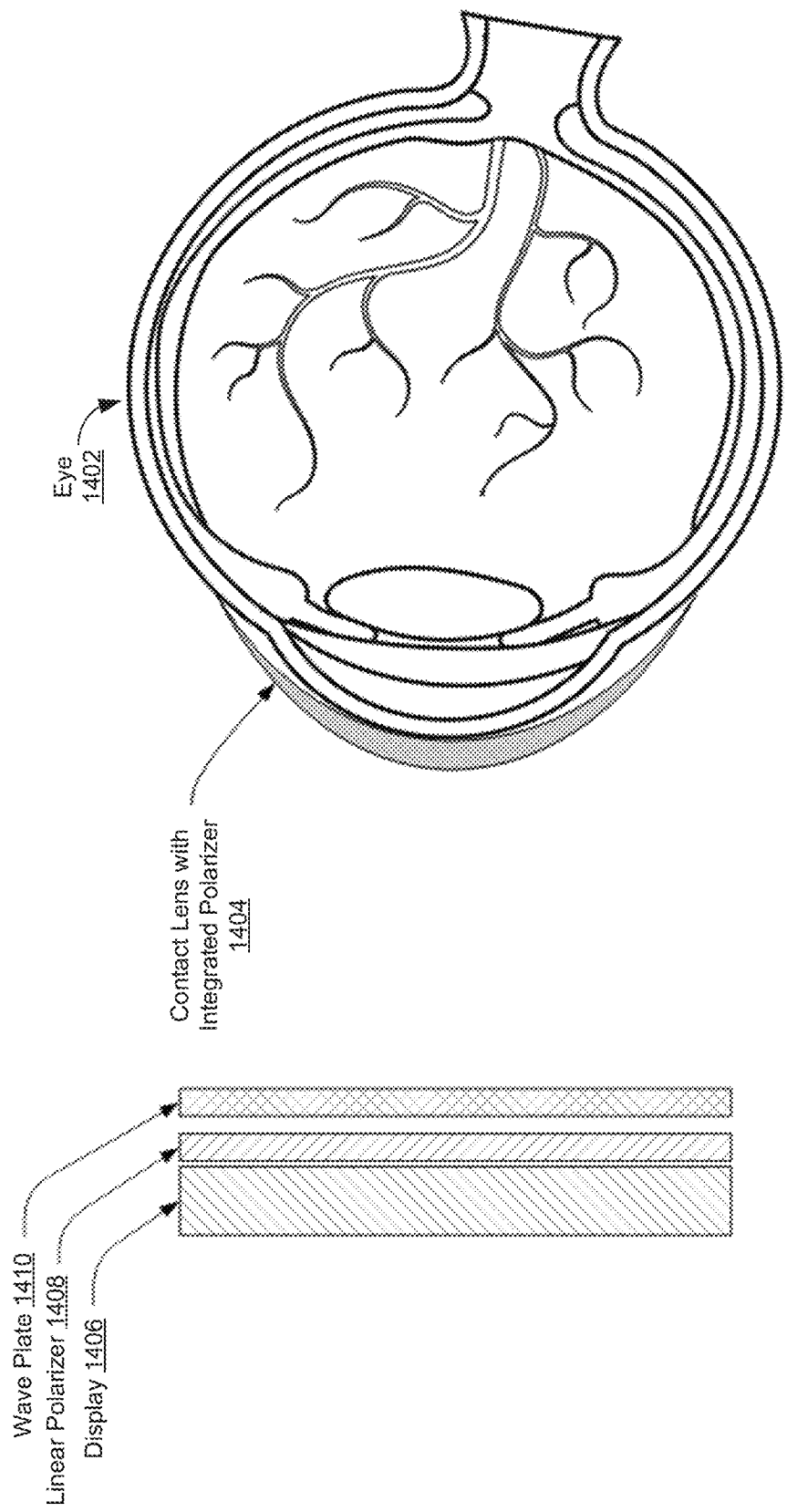
FIG. 14 illustrates a side view of a system that includes a contact lens with a integrated polarizer disposed upon an eye and a display, linear polarizer, and a wave plate.
Figure 15:
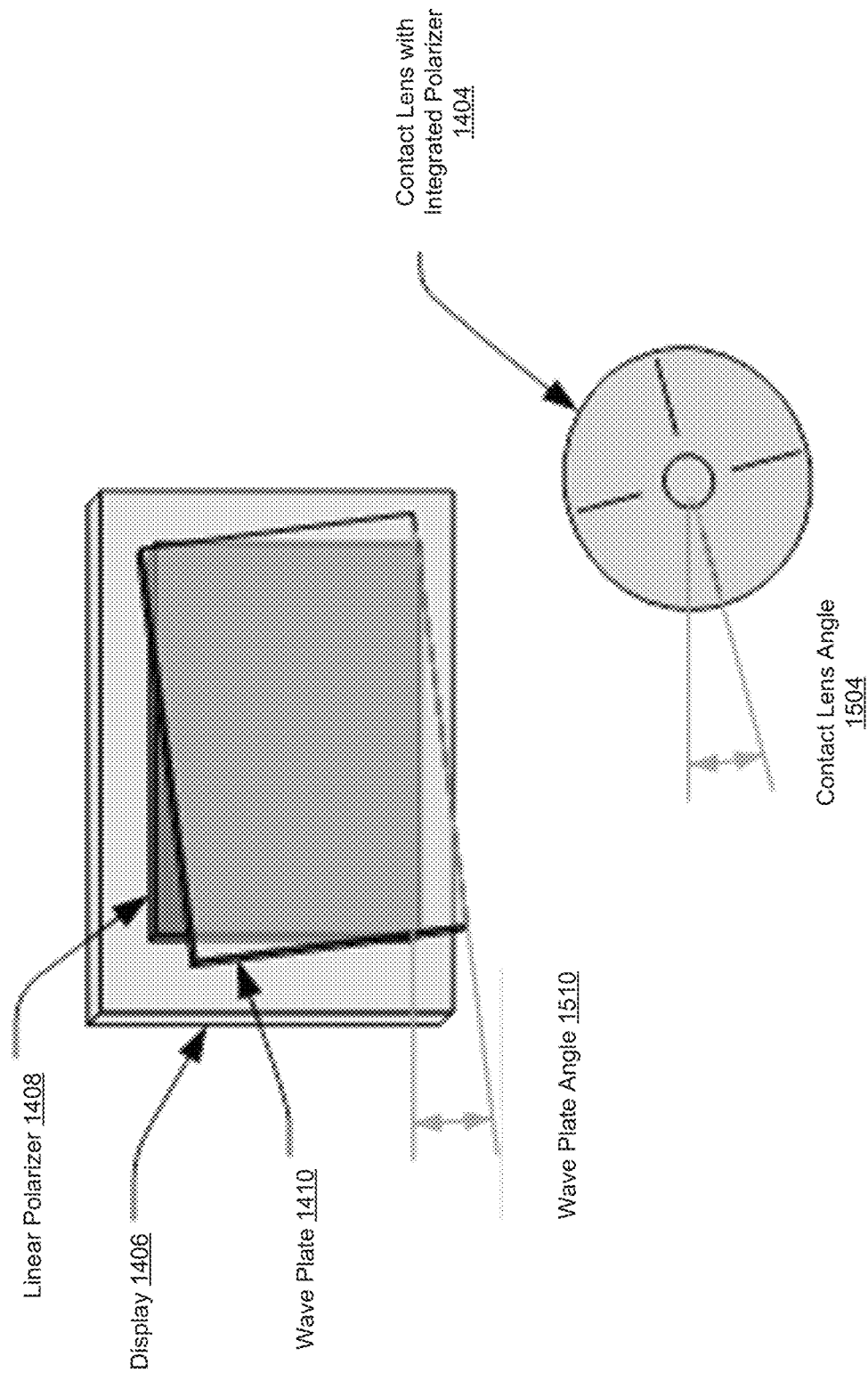
FIG. 15 illustrates a user's view of the system of FIG. 14, along with the wave plate angle and the contact lens angle.

FIG. 14 illustrates a side view of a system that includes a contact lens with a integrated polarizer 1404 disposed upon an eye 1402 and a display 1406, linear polarizer 1408, and a wave plate 1410. In some embodiments, the light emitted by the display 1406 may already be polarized, as with Liquid Crystal Display (LCD) and Liquid Crystal on Silicon Display (LCoS) technologies. In such embodiments, the linear polarizer 1408 may be omitted. FIG. 15 illustrates a user's view of the system of FIG. 14, along with the wave plate angle 1510 and the contact lens angle 1504. In some embodiments, the light emitted by the display 1406 may already be polarized, as with Liquid Crystal Display (LCD) and Liquid Crystal on Silicon Display (LCoS) technologies. In some embodiments, such systems may be combined with the display position and pixel shifting features describe herein based on eye and head scanned metrics.

Conventional head scanners and imagers cannot detect the corneal surface because it is transparent. Instead, these devices tend to detect the iris, and therefore the eye in the resulting image looks caved-in. Some embodiments of the disclosure provide systems and methods for automated contact lens and eyewear frame design using physical landmarks placed on the eye. The physical landmarks enable the acquisition of high-quality corneal surface topology and sagittal depth measurement from the apex of the cornea to at least one semi-meridian radial distance outside the cornea. To be clear, the surface topology would not be possible without the physical landmark placed on the eye. These techniques are also applicable to imaging the sclera of the eye simultaneously with the transparent cornea of the eye. These images may be used to determine parameters for the design of eyeglasses, display eyewear, and contact lenses for use with or without the display eyewear.

Figure 16:
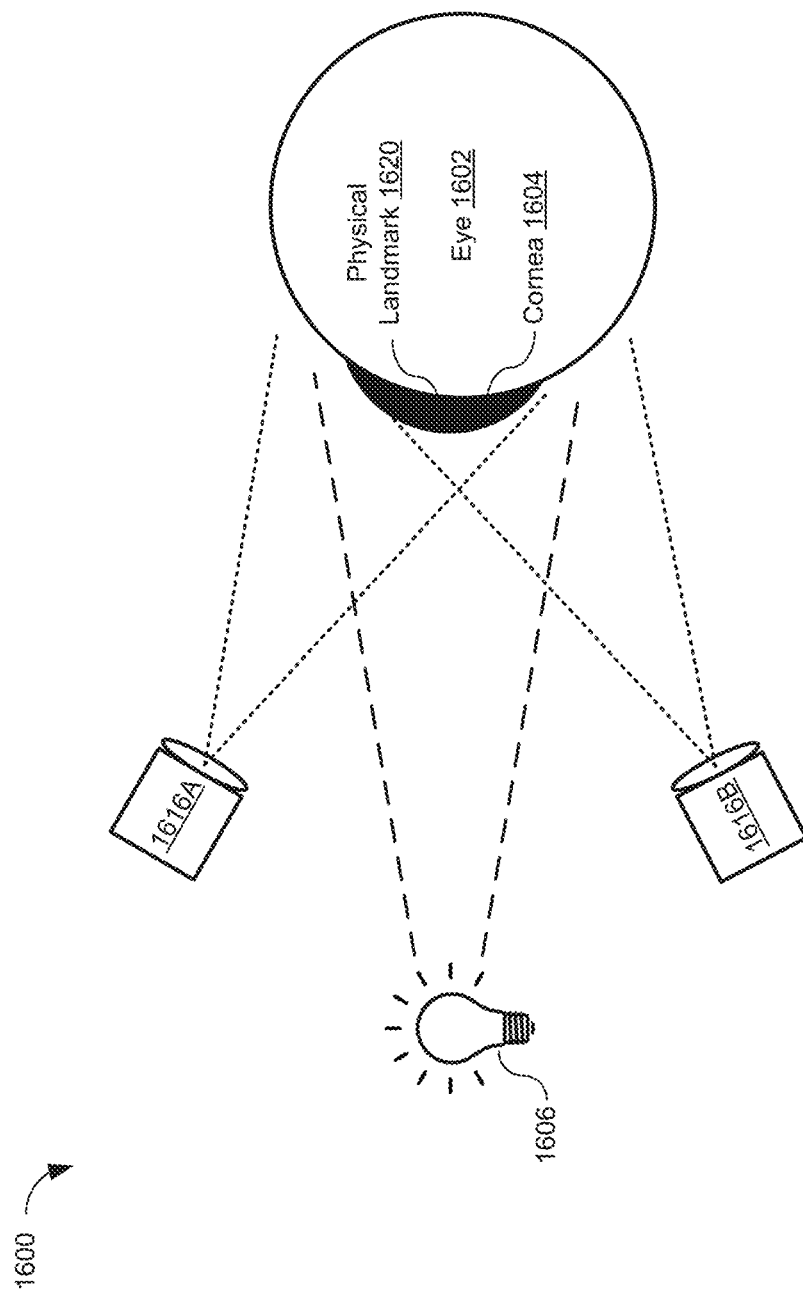
FIG. 16 illustrates an image capture system for capturing images of the eye of a user while wearing a measurement contact lens according to some embodiments of the disclosed technology.

FIG. 16 illustrates an image capture system 1600 for capturing images of the eye of a user while wearing a measurement contact lens according to some embodiments of the disclosed technology. Referring to FIG. 16, the eye 1602 is shown, as well as the cornea 1604 of the eye. Also shown is a physical landmark 1620 disposed upon the eye 1602. The image capture system 1600 may include a light source 1606 and one or more cameras 1614A,B, which may be positioned on opposite sides of the light source 1606. With the light source 1606 on and illuminating the eye 1602, each camera 1614 may capture one or more images of the eye 1602 and the physical landmark 1620.

Figure 17:
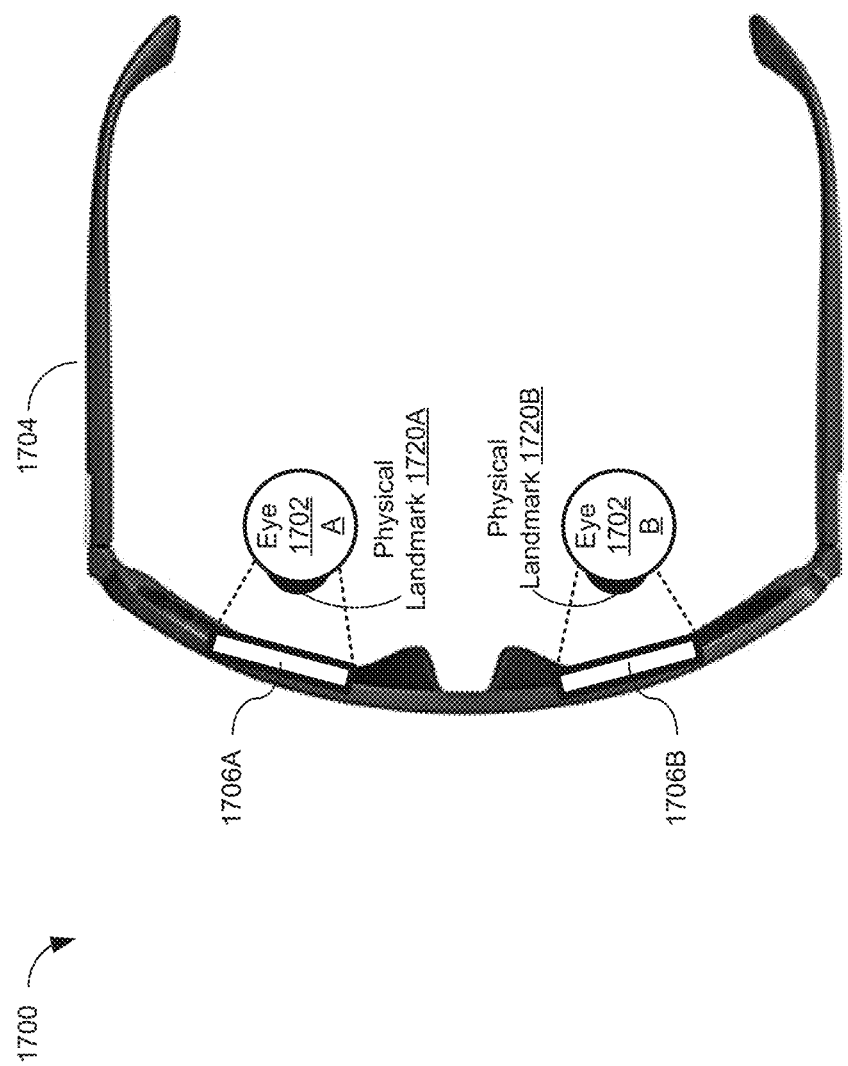
FIG. 17 illustrates an embodiment where the elements of the image capture system of FIG. 16 may be arranged in measurement eyewear.

The elements of the image capture system 1600 of FIG. 16 may be arranged in a variety of multifunction devices. In some embodiments, the elements of the image capture system 1600 of FIG. 16 may be arranged in measurement eyewear, for example such as a pair of spectacles. FIG. 17 illustrates one such embodiment. Referring to FIG. 17, a multifunction device 1700 includes a pair of spectacles 1704 and two image capture systems 1706A,B arranged to capture images of the user's eye's 1702A,B while physical landmarks 1720A,B are on the eyes 1702A,B, respectively. In these embodiments, the measurement eyewear is disposed on the face of the user prior to capturing the images.

A control system (not shown) to control the image capture subsystems 1706 may be included in the multifunction device 1700, may be located externally to the multifunction device 1700, or a combination thereof. In embodiments where some or all of the control system is external to the multifunction device 1700, the multifunction device 1700 may include a receiver or transceiver for connecting the multifunction device 1700 to the external elements.

Figure 18:
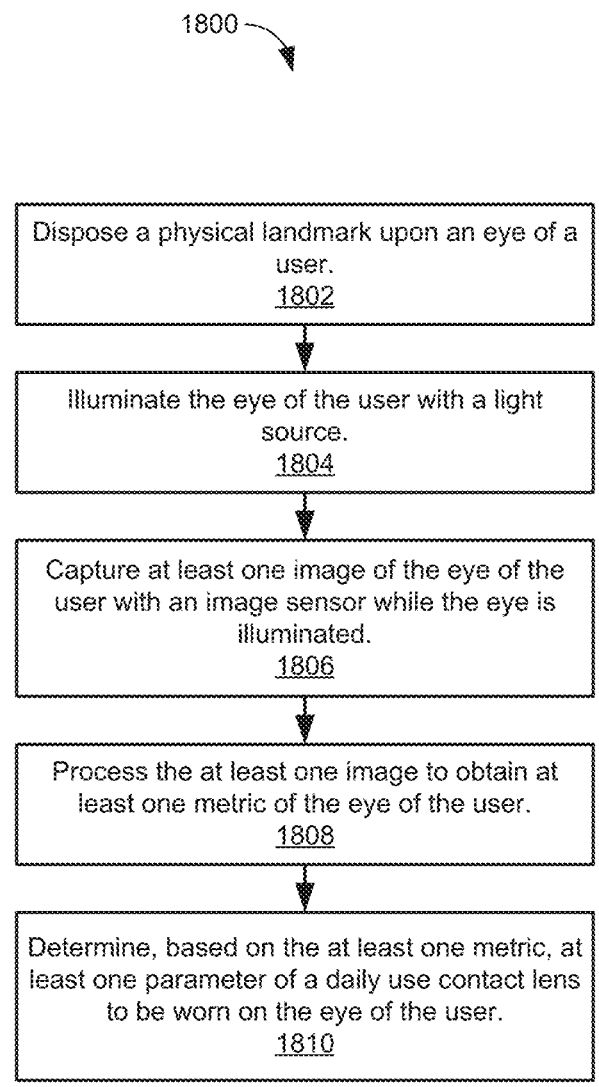
FIG. 18 is a flowchart illustrating a process for automated contact lens design through image capture of the eye wearing a reference contact lens according to some embodiments of the disclosed technology.

FIG. 18 is a flowchart illustrating a process 1800 for automated contact lens design through image capture of the eye wearing a reference contact lens according to some embodiments of the disclosed technology. The elements of the process 1800 are presented in one arrangement. However, it should be understood that one or more elements of the process may be performed in a different order, in parallel, omitted entirely, and the like. Furthermore, the process 1800 may include other elements in addition to those presented.

Referring to FIG. 18, the process 1800 may include disposing a physical landmark 1620 upon an eye of a user, at 1802. In some embodiments, the physical landmark 1620 is a measurement contact lens. In some embodiments, the measurement contact lens includes orientation marks, for example such as those described elsewhere in this description. In other embodiments, the measurement contact lens has no orientation marks. In some embodiments, the measurement contact lens conforms to the shape of the eye of the user. In some embodiments, the measurement contact lens is not opaque to the image sensor. The thickness profile of the measurement contact lens that conforms to the shape of the eye is known. The shape of the eye may be determined by subtracting the known thickness profile of the measurement contact lens from the dimensions measured by scanning or imaging. In some embodiments, the physical landmark 1620 is a liquid film comprised of materials that are visible to the image sensor. In some embodiments, the physical landmark may include a biocompatible ophthalmic dye like gentian violet or trypan blue. Other physical landmarks including liquids formulated with suspended particles or dissolved colorants are contemplated.

The cameras 1614 may operate in the visible light spectrum, or in other spectra. The physical landmarks may be selected to be visible to the cameras 1614 in the spectra in which the cameras 1614 operate. For example, the liquid film may reflect light in the spectrum of the image sensor.

Referring again to FIG. 18, the process 1800 may include illuminating the eye of the user with a light source, at 1804, and capturing at least one image of the eye of the user with an image sensor while the eye is illuminated, at 1806. For example, referring again to FIG. 16, the eye 1602 of the head and eye of the user may be illuminated by the light source 1606 of the image capture system 1600, and each camera 1614A,B may capture one or more images of the eye 1602 while the eye 1602 is illuminated and the physical landmark 1620 is on the eye 1602. The captured images therefore include images of the physical landmark. The captured images may include at least one other point on the surface of the eye 1602 outside of the cornea 1604. In embodiments where the measurement contact lens includes orientation marks, the captured images may include images of the orientation marks. The images may include features of the eye such as the pupil, the visible iris, the cornea, the sclera, and the eyelids. In other embodiments, ambient light may be used to illuminate the eye, and no other light sources are used.

Referring again to FIG. 18, the process 1800 may include processing the at least one image to obtain at least one metric of the eye of the user, at 1808. The metrics may include those described elsewhere in this description. For example, the metrics may include the sagittal depth of at least one semi chord radial distance from the apex of the cornea, the diameter of the pupil, the horizontal visible iris or corneal diameter, the position of the eyelids, the height of the aperture between the lids, and similar metrics. In some embodiments, this processing may include the use of artificial intelligence techniques, for example as described above.

In some embodiments, the measurement eyewear may be display eyewear, for example as described and illustrated elsewhere in the description and drawings. In these embodiments, the metrics may include a vertex distance between an apex of a cornea of the eye and the display, a distance between the centers of the pupils, a vertical position of the center of the pupil relative to the center of the display, and similar metrics.

Referring again to FIG. 18, the process 1800 may include determining, based on the at least one metric, at least one parameter of a contact lens to be worn on the eye of the user, at 1810. Contact lenses may then be manufactured or selected from a collection of lenses based on the parameters. For example, the parameters may include those depicted in, and discussed with reference to, FIG. 8. This process may also be used to determine parameters of other eyewear, including spectacles and display eyewear, for example as described elsewhere in this description.

For display eyewear, the parameters may be employed to determine an amount of image shifting to be employed in the images displayed. Techniques for electronic and optical image shifting in display eyewear are described in related U.S. patent application Ser. No. 18/915,985, filed Jun. 31, 2220, entitled "DISPLAY EYEWEAR WITH ADJUSTABLE CAMERA DIRECTION," the disclosure thereof incorporated by reference herein in its entirety.

Figure 19B:
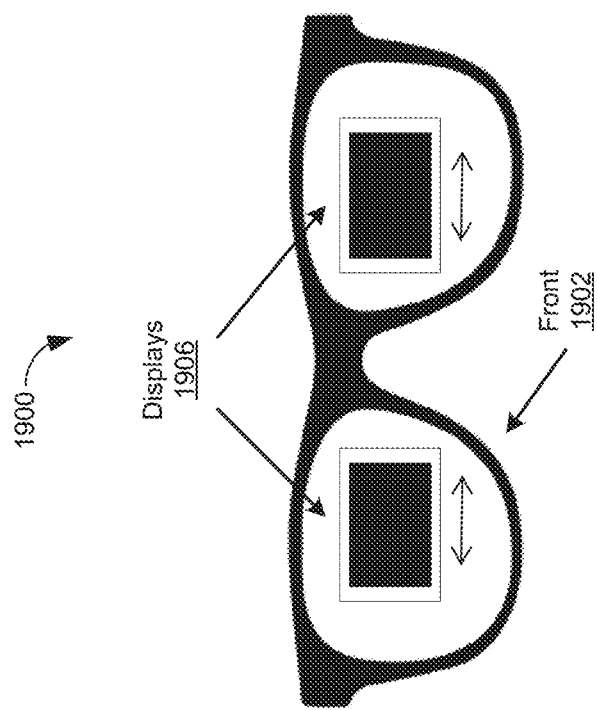
FIGS. 19A,B illustrate display eyewear according to some embodiments of the disclosed technology.
Figure 19A:
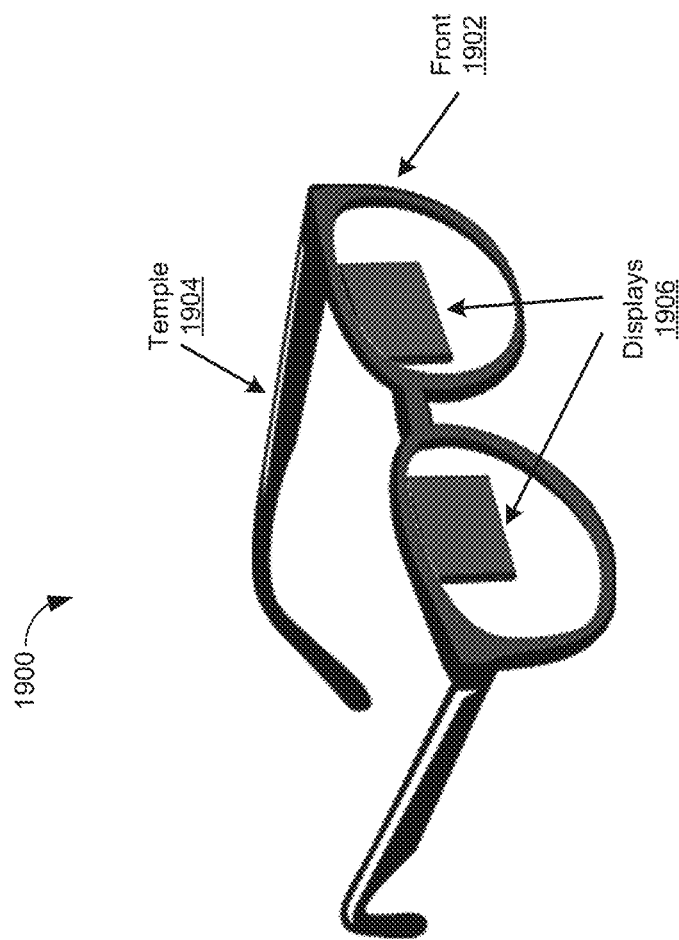

In some embodiments, rather than shifting the image within the display, the display itself may be shifted, for example by mechanical means. FIGS. 19A,B illustrate display eyewear 1900 according to some embodiments of the disclosed technology. Referring to FIG. 19A, the display eyewear includes front 1902, temples 1904, and displays 1906. In the described embodiments, the displays 1906 may be shifted horizontally, as shown in FIG. 19 B. In other embodiments, the displays 1906 may be shifted horizontally, vertically, in other directions, or any combination thereof.

FIGS. 20A,B,C illustrate mechanisms for adjusting eyewear displays horizontally according to some embodiments of the disclosed technology. FIG. 20A illustrates a pair of mechanically adjustable displays 2002A,B according to some embodiments of the disclosed technologies. The mechanically adjustable displays 2002A,B include displays 2012A,B, respectively, and may be used for example as the displays 1906 in the display eyewear 1900 of FIGS. 19A,B. FIG. 20B is a side view of one of the adjustable displays 2002. Referring to FIG. 20B, the adjustable displays 2002 may be attached to the front of the display eyewear 1900 with a friction clamp 2012 or similar mechanism.

FIG. 20C illustrate details of the mechanisms according to some embodiments of the disclosed technology. Referring to FIG. 20C, the display 2002B for the user's left eye is shown in three positions corresponding to the user's left, center and right. The adjustable display 2002B includes the display 2012B, two edge guides 2004A,B, an adjuster cam 2006, a spring 2008, and a spring base 2010. The spring 2008 is disposed between the spring base 2010 and the display 2012B. The spring 2008 biases the display 2012B against the adjuster cam 2006. As the adjuster cam 2006 is rotated, the display 2012B moves horizontally within the edge guides 2004A,B. In some embodiments, the adjuster cam 2006 may be rotated by an electric motor or the like. In other embodiments, the adjuster cam 2006 may be rotated manually.

Figure 21:
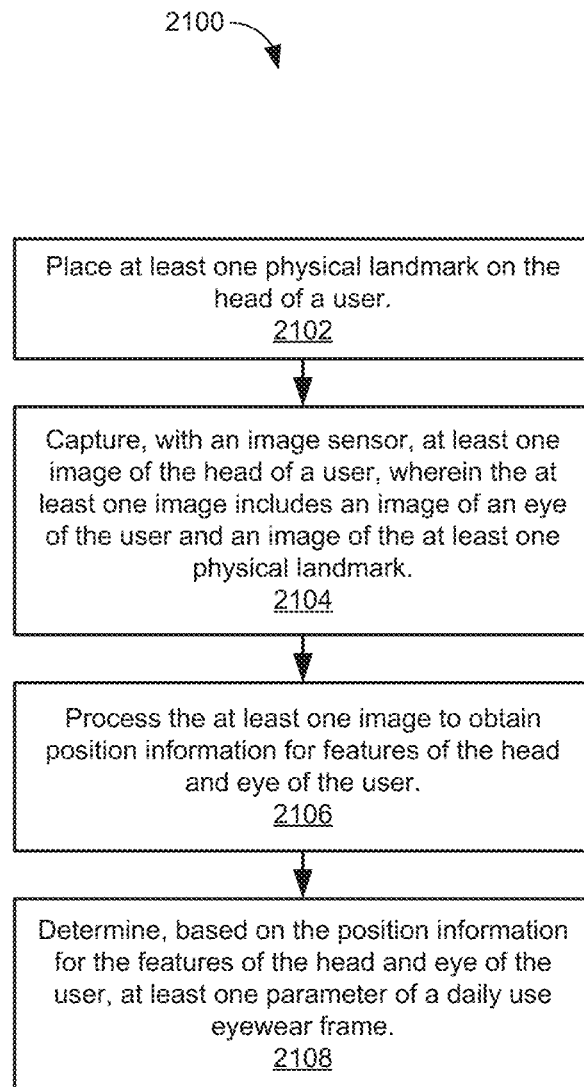
FIG. 21 is a flowchart illustrating a process for automated eyewear frame design through image capture of landmarks placed on the user's eye and head according to some embodiments of the disclosed technology.

Some embodiments of the disclosure provide systems and methods for automated eyewear frame design through image capture of landmarks placed on the user's eye and head. FIG. 21 is a flowchart illustrating a process 2100 for automated eyewear frame design through image capture of landmarks placed on the user's eye and head according to some embodiments of the disclosed technology. The elements of the process 2100 are presented in one arrangement. However, it should be understood that one or more elements of the process may be performed in a different order, in parallel, omitted entirely, and the like. Furthermore, the process 2100 may include other elements in addition to those presented.

Referring to FIG. 21, the process 2100 may include placing at least one physical landmark on the head of a user, at 2102, and capturing, with an image sensor, at least one image of the head of a user, wherein the at least one image includes an image of an eye of the user and an image of the at least one physical landmark, at 2104. In some embodiments, physical landmarks may be placed on the eye of the user as well, for example as described elsewhere in this description.

Figure 22:
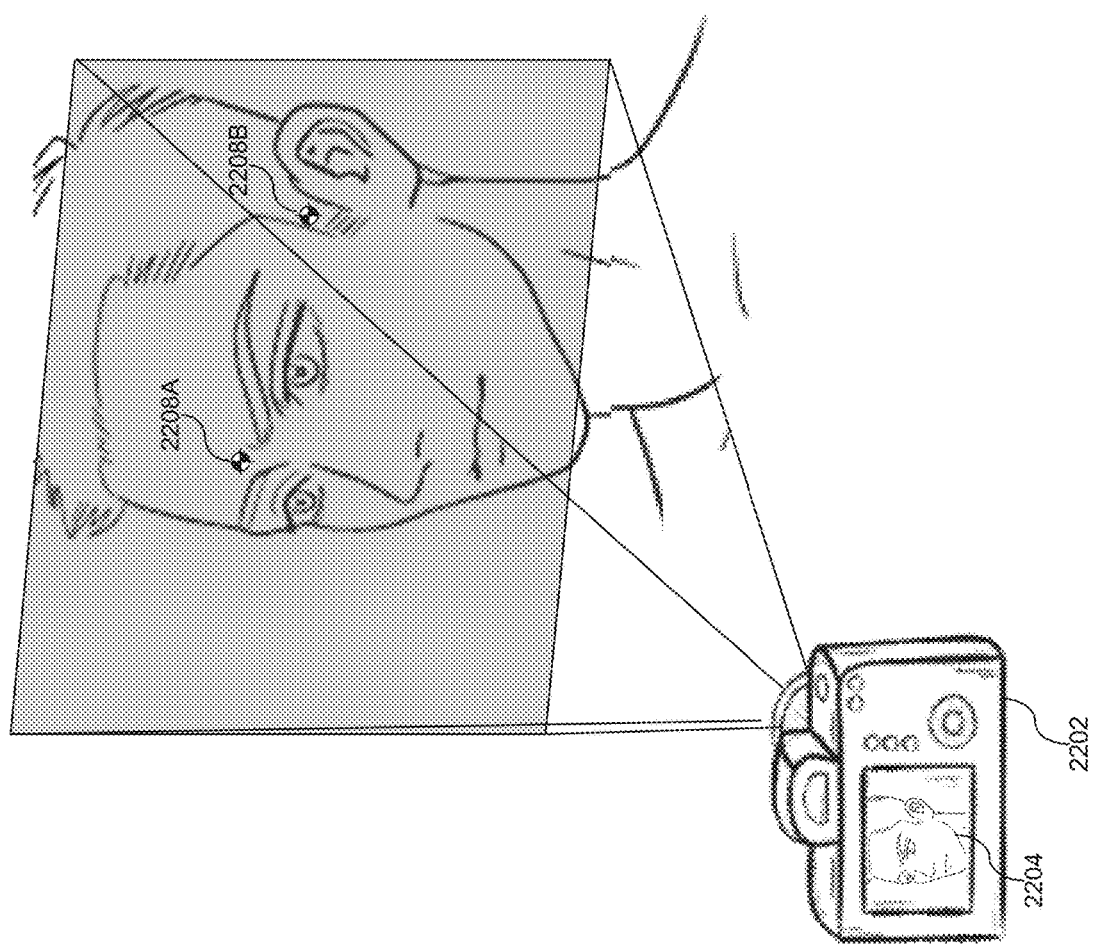
FIG. 22 illustrates the capture of an image of the user with physical landmarks placed on the user's head according to some embodiments of the disclosed technology.

FIG. 22 illustrates the capture of an image of the user with physical landmarks placed on the user's head according to some embodiments of the disclosed technology. Referring to FIG. 22, a physical landmark in the form of a sticker 2208A has been placed on the user's forehead, and another sticker 2208B has been placed near the user's left ear. However, it should be understood by those skilled in the relevant arts that any type and number of physical landmarks may be employed. In the example of FIG. 22, the image capture device used to capture the image 2204 of the user is a conventional digital camera 2202. However, it should be understood by those skilled in the relevant arts that any suitable image capture device may be used.

Referring again to FIG. 21, the process 2100 may include processing the at least one image to obtain position information for features of the head and eye of the user, at 2106. The position information may be obtained according to the image of the at least one physical landmark. In some embodiments, this processing may include the use of artificial intelligence techniques, for example as described above.

Figure 23:
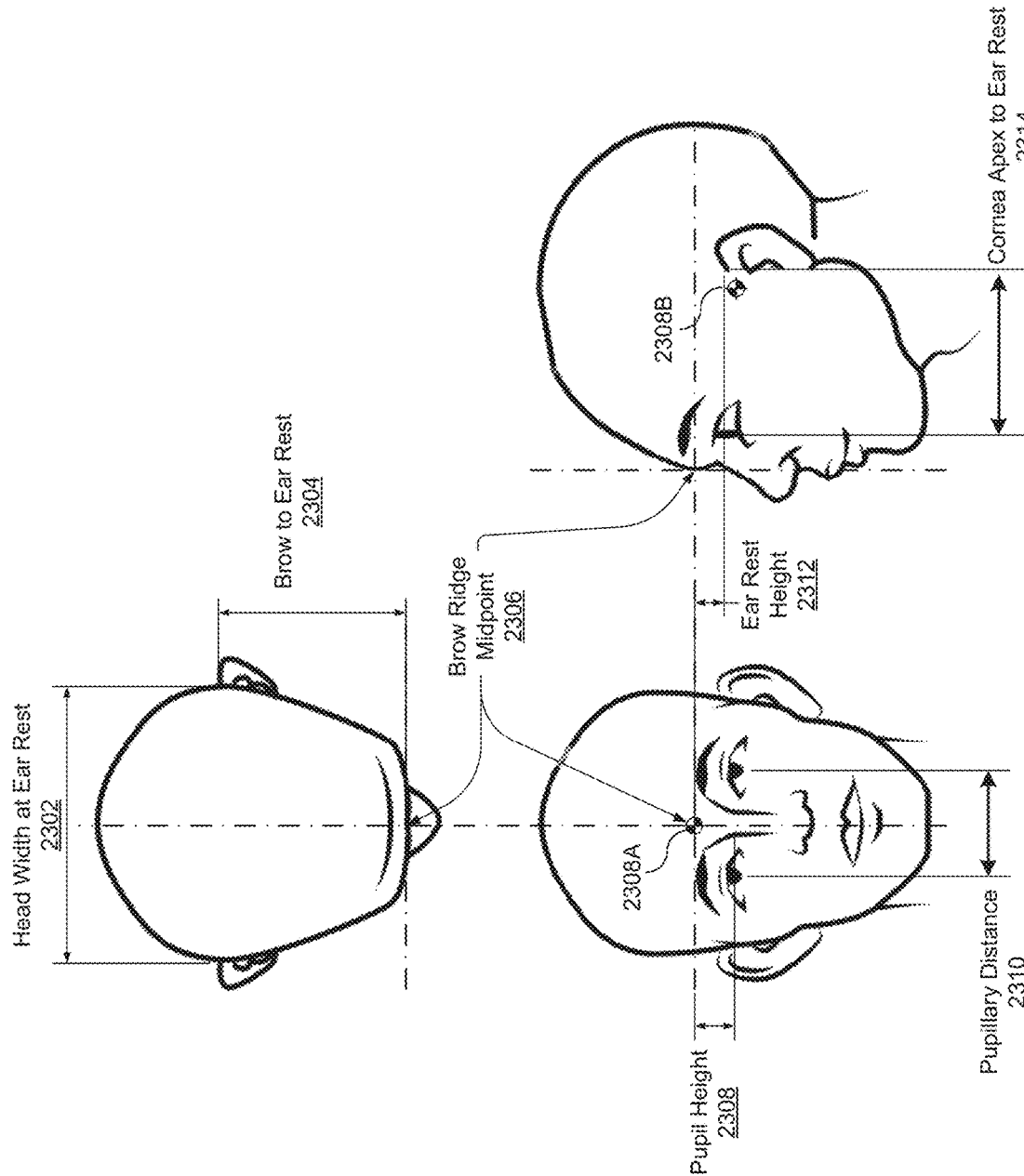
FIGS. 23 and 24A,B illustrate example position information that may be obtained from a captured image of the user's head according to an image of a user's head including physical landmarks.
Figure 24B:
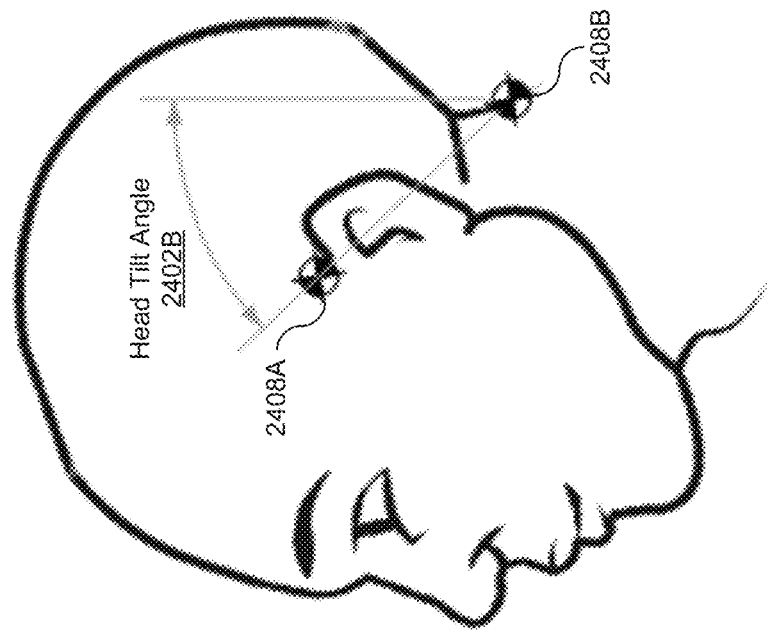
Figure 24A:
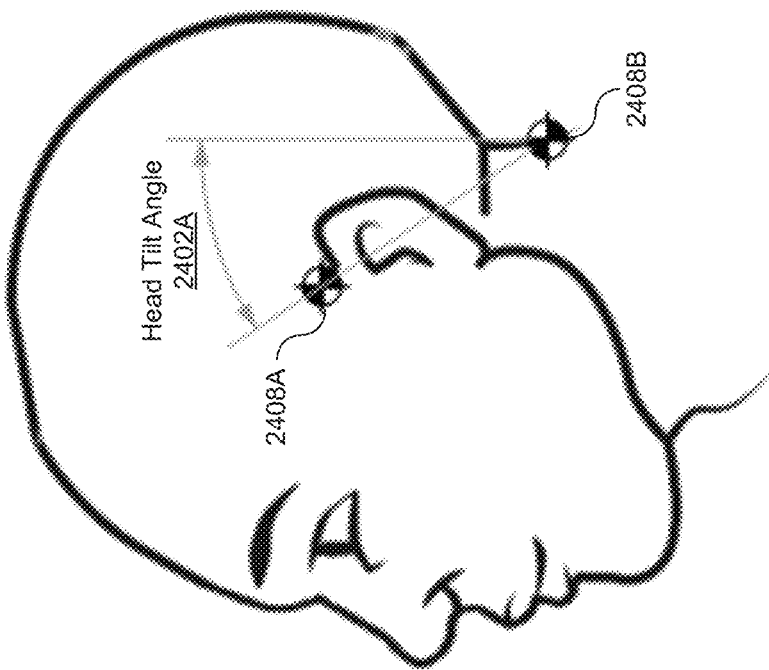

FIGS. 23 and 24A,B illustrate example position information that may be obtained from a captured image of the user's head according to an image of a user's head including physical landmarks. Referring to FIG. 23, three views of the user's head are depicted, including a top view, a front view, and a side view. Also shown are two physical landmarks in the form of stickers 2308A,B disposed upon the user's head. The example position information shown in FIG. 23 includes a width of the user's head at the ear rest 2302, a distance between the brow and the ear rest 2304, a location of the brow ridge midpoint 2306, a pupil height 2308, a pupillary distance 2310, an ear rest height 2312, and a distance between the cornea apex to the ear rest position 2314. Other position information is contemplated.

Referring to FIGS. 24A,B, two side views of a user's head are depicted, including physical landmarks 2408A,B placed near the user's ear, and on the user's neck, respectively. The neck landmark 2408B may be placed on the highest vertebrae that does not move when the subject tilts their head. From images of the user's head and the physical landmarks 2408, one or more head tilt angles may be determined. Note that the head tilt angle changes when the individual changes activity from straight ahead viewing to desk tasks and to normal reading positions. FIG. 24A depicts a resting head tilt angle 2402A, while FIG. 24B depicts a reading head tilt angle 2402B. These metrics may be used to select a pantoscopic tilt, camera angle, and/or display angle for the user.

Figure 25:
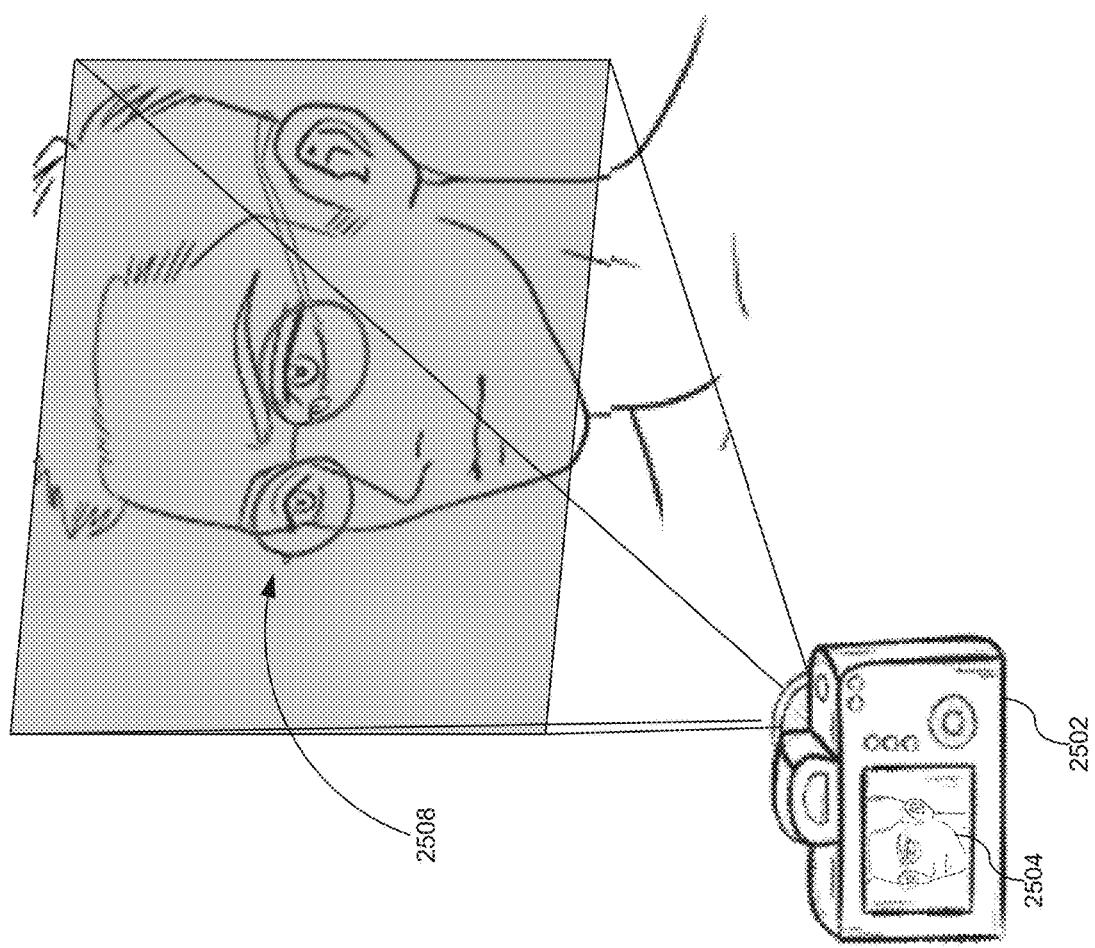
FIG. 25 illustrates the capture of an image of a user wearing diagnostic eyewear according to some embodiments of the disclosed technology.

In some embodiments, the physical landmarks may take the form of diagnostic eyewear. FIG. 25 illustrates the capture of an image of a user wearing diagnostic eyewear according to some embodiments of the disclosed technology. In the example of FIG. 25, the diagnostic eyewear takes the form of a pair of eyeglasses 2508. In the example of FIG. 25, the image capture device used to capture the image 2504 of the user is a conventional digital camera 2502. However, it should be understood by those skilled in the relevant arts that any suitable image capture device may be used.

Figure 26:
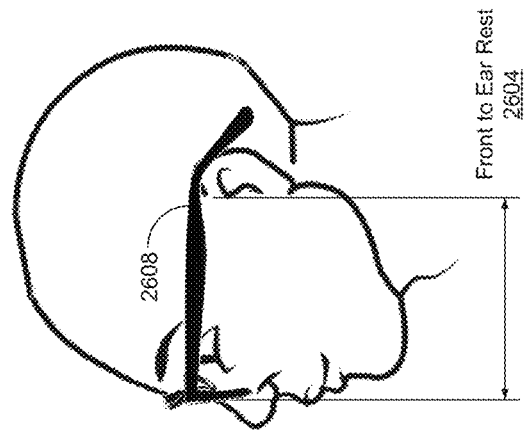
FIG. 26 illustrates example position information that may be obtained from a captured image of the user's head according to an image of a user's head including diagnostic eyewear.
Figure 26:
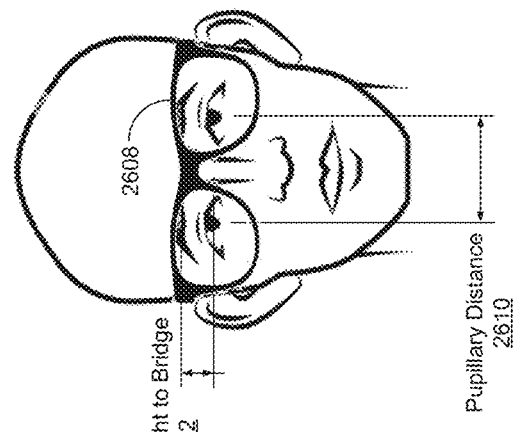

FIG. 26 illustrates example position information that may be obtained from a captured image of the user's head according to an image of a user's head including diagnostic eyewear. Referring to FIG. 26, two views of the user's head are depicted, including a front view and a side view. Also shown is diagnostic eyewear 2608 disposed upon the user's head. The example position information shown in FIG. 26 includes a pupillary height 2602 between the pupil of the user's eye and the bridge of the diagnostic eyewear 2608, a distance 2604 between the front to the diagnostic eyewear 2608 and the ear rest, and a pupillary distance 2610.

Figure 27:
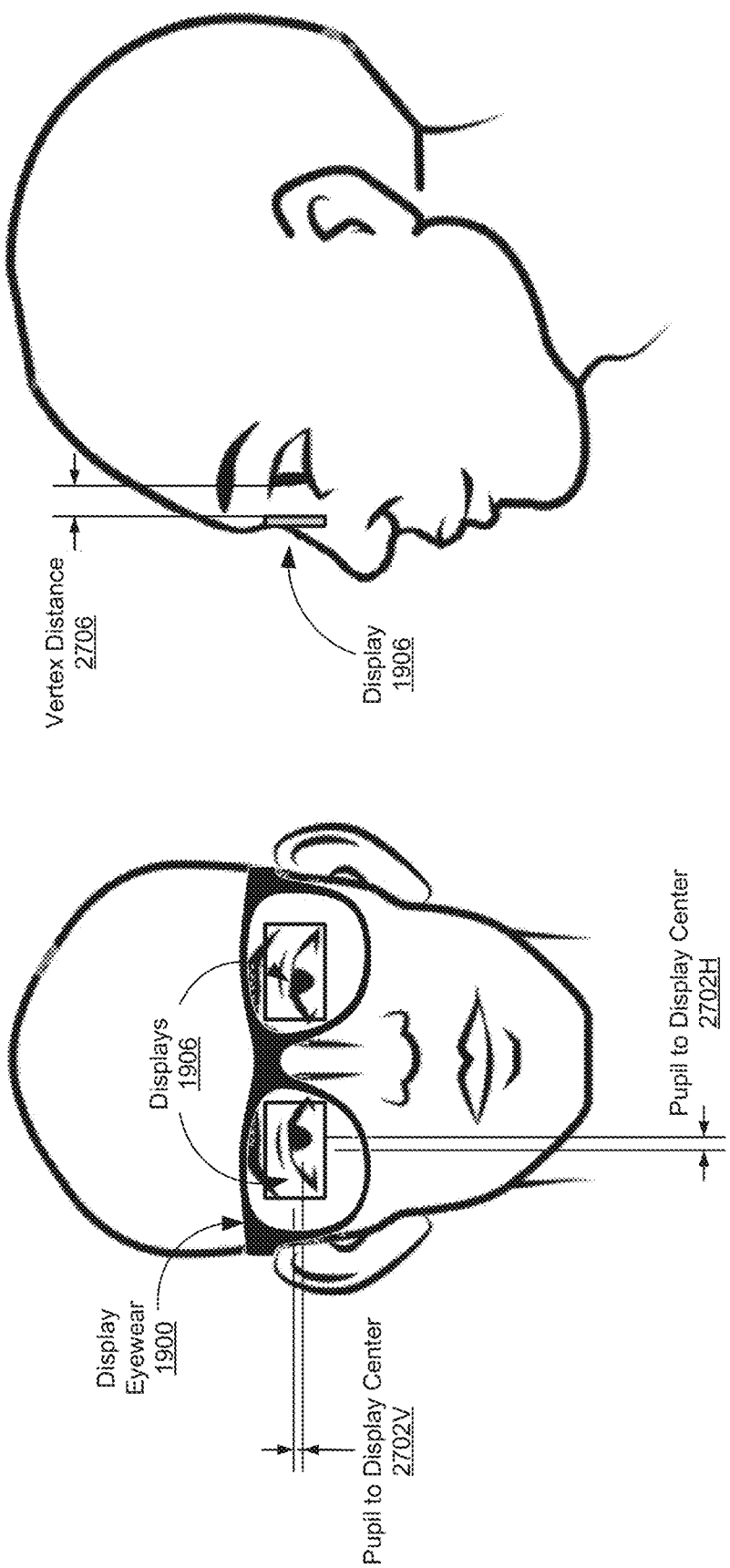
FIG. 27 illustrates example position information that may be obtained from a captured image of the user's head according to an image of a user's head including display eyewear.

In some embodiments, the physical landmarks may take the form of display eyewear, for example such as the display eyewear 1900 of FIGS. 19A,B. FIG. 27 illustrates example position information that may be obtained from a captured image of the user's head according to an image of a user's head including display eyewear. Referring to FIG. 27, two views of the user's head are depicted, including a front view and a side view. Also shown is display eyewear 1900 disposed upon the user's head. The example position information shown in FIG. 27 includes vertical and horizontal distances 2702V,H between the pupil of the user's eye and the center of display 1906, and a vertex distance between display 1906 and the apex of the cornea of the user's eye. In some embodiments, the display 1906 may be fully functional. In some embodiments, the display 1906 may be partially functional or non-functional, and used for measurement purposes only.

Figure 28:
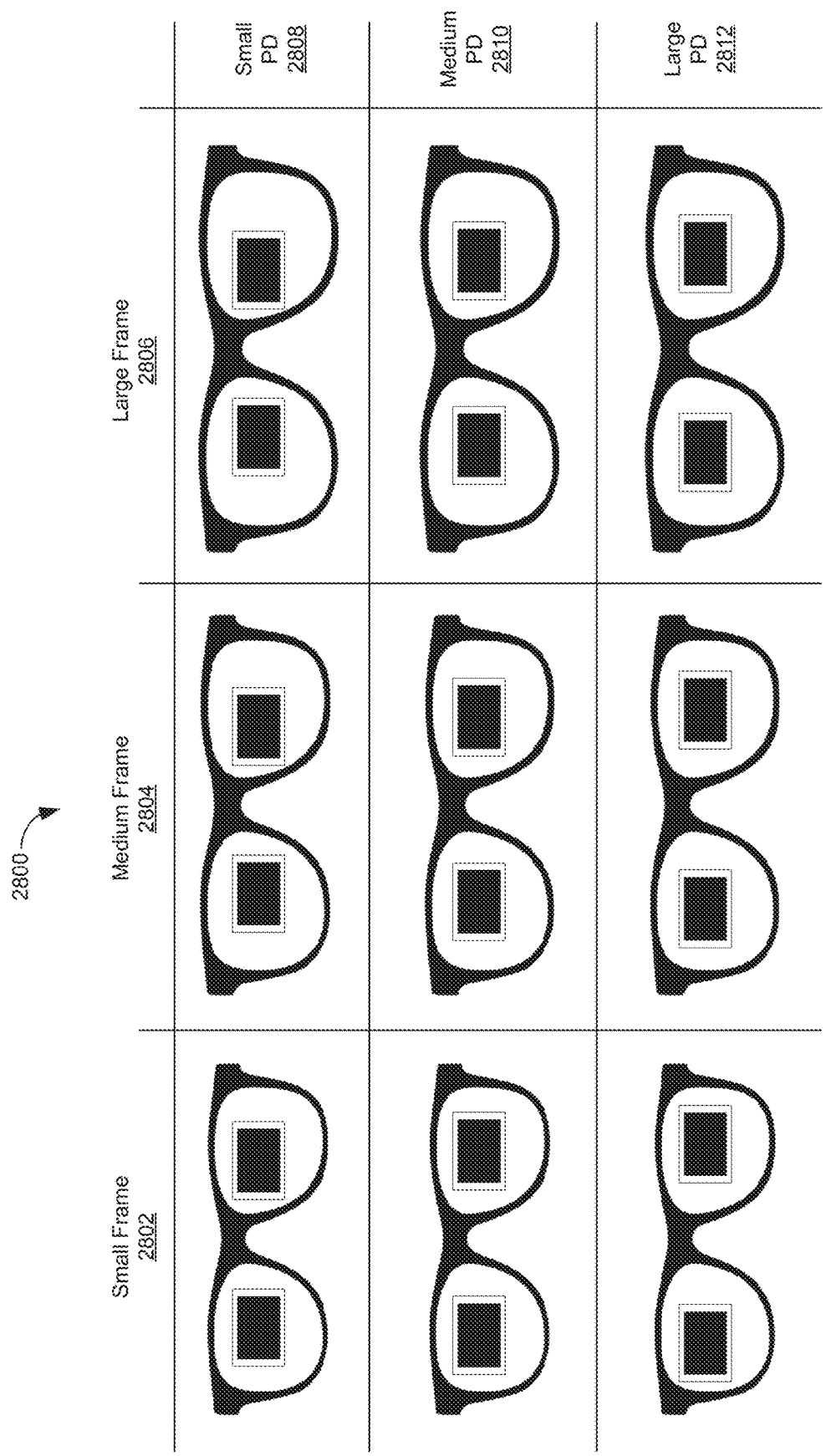
FIG. 28 illustrates a collection of display eyewear that includes nine stock keeping units derived from combinations of three frame sizes and three display locations.

Referring again to FIG. 21, the process 2100 may include determining, based on the position information for the features of the head and eye of the user, at least one parameter of a daily use eyewear frame, at 2108. Eyewear frames may then be manufactured based on the parameters or selected from a collection of pre-fabricated eyewear, or assembled from a collection of pre-fabricate sub-parts. The parameters may include the size of the front of a pair of display eyewear and locations of displays relative to the front. FIG. 28 illustrates a collection 2800 of display eyewear that includes nine stock keeping units derived from combinations of three frame sizes and three display locations. Referring to FIG. 28, the collection 2800 includes three frame sizes including a small frame 2802, a medium frame 2804, and a large frame 2806. The collection 2800 also includes three display locations based on the user's pupillary distance (PD) including a small PD 2808, a medium PD 2810, and a large PD 2812.

FIG. 29 is an example data structure 2900 for determining parameters of display eyewear for a user based on the user's metrics. In particular, the data structure 2900 may be used to determine a frame size based on pupillary distance and head width. In this example, the frame sizes include small (S), medium (M), and large (L).

Figure 30:
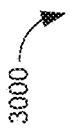
FIG. 30 is another example data structure for determining parameters of display eyewear for a user based on the user's metrics.

FIG. 30 is another example data structure 3000 for determining parameters of display eyewear for a user based on the user's metrics. In addition to having frame sizes, each frame has a range of display positions. These positions may be continuously adjustable, may have a pre-defined discrete set points, or a combination thereof. The data structure 3000 provides an example of how the ranges might be configured with only the limits and midpoint for display position being defined.

If a particular frame design requires a display position to be placed at a discrete position or at an extreme limit, another adjustment may be implemented to expand the reach of the fitting range. This adjustment may be achieved by shifting the digital images on the displays to help align the digital images with the users' eye positions.

The digital shifting of the image from the geometric center of the display may result in three zones for the user: a left monocular zone, a central binocular zone, and a right monocular zone. The amount of binocular overlap, defined in degrees or percentage of display image, is important for user comfort and has lower boundaries. The extremes are easily defined at 100% and 0%, and these are technically valid, but it is more common to have a lower threshold of overlap of 50% for small displays and 32 degrees of overlap for larger displays.

In some embodiments, the process may prescribe the amount of digital image shifting as a limit on physical center to center distance shifting. For example, a pair of displays that are at the extremes of adjustment but fail to align with the users eyes by 1 mm center to center (i.e., 64 mm PD, 65 mm display centers), would be able to use 1 mm of total image shifting, or 0.5 mm on each display, to bring the digital centers into alignment with the users eyes.

The data structure 3000 provides three examples of small, medium, and large displays. In each case, the variety of digital image shifting may be controlled as a percentage of micro-display screen width (33%, 50%, and 66%) to reflect how a single parameter of display width percentage could be used to influence the alignment and performance of the system. The available display center to user PD adjustment range is represented by the heading "Display Width Shift (C to C)" while the system performance at the boundary of this range is represented by the resulting "Display Overlap Angle" and "Display Overlap %". Row number 2 along with the columns identified by "33%" are used as the basis for the data structure 2900.

In these embodiments, the process may combine certain anthropomorphic data with frame size data and display adjustment systems (both digital and mechanical) to quickly select which frame would be a best fit for a user's head size and PD. The temple arm length and pantoscopic tilt are more directly derived from the head scan data and the available frame designs, and these may require a similar process when the temple length and pantoscopic tilts are fixed with component selection and not otherwise adjustable at the time of dispensing.

Figure 31:
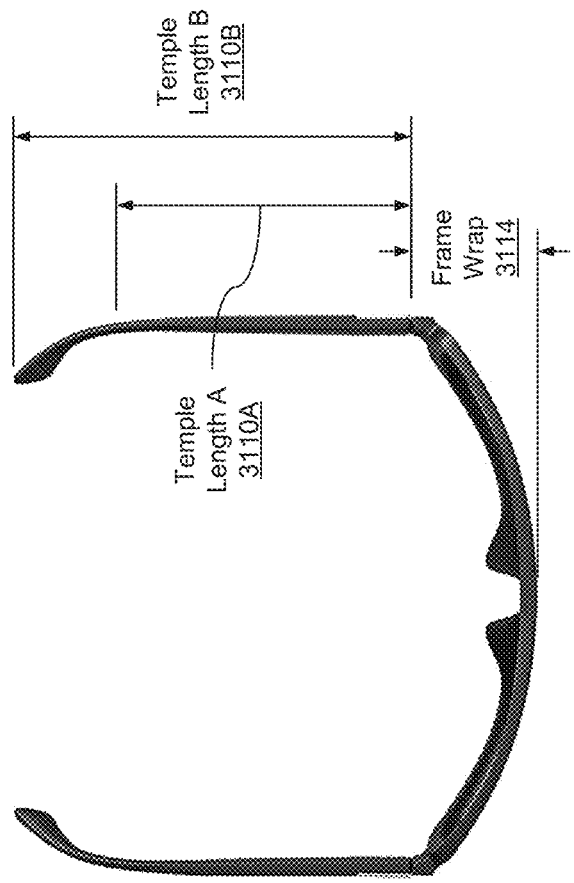
FIG. 31 illustrates other eyeglass parameters that may be determined based on the obtained position information.
Figure 31:
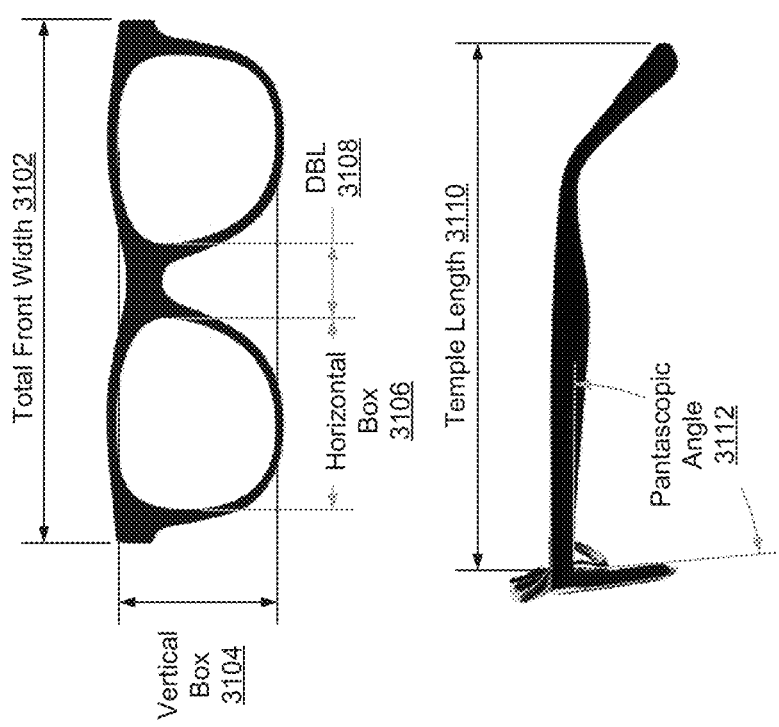

FIG. 31 illustrates other eyeglass parameters that may be determined based on the obtained position information. Referring to FIG. 31, three views of a pair of eyeglasses are shown, including a front view, a side view, and a top view. Referring to the front view, the parameters may include a total width 3102 of the front, a vertical box dimension 3104, horizontal box dimension 3106, and a distance between lenses (DBL) 3108. Referring to the side view, the parameters may include a temple length 3110, and a pantoscopic angle 3112. A temple length A 3110A, a temple length B 3110B, and a frame wrap 3114.

Figure 32:
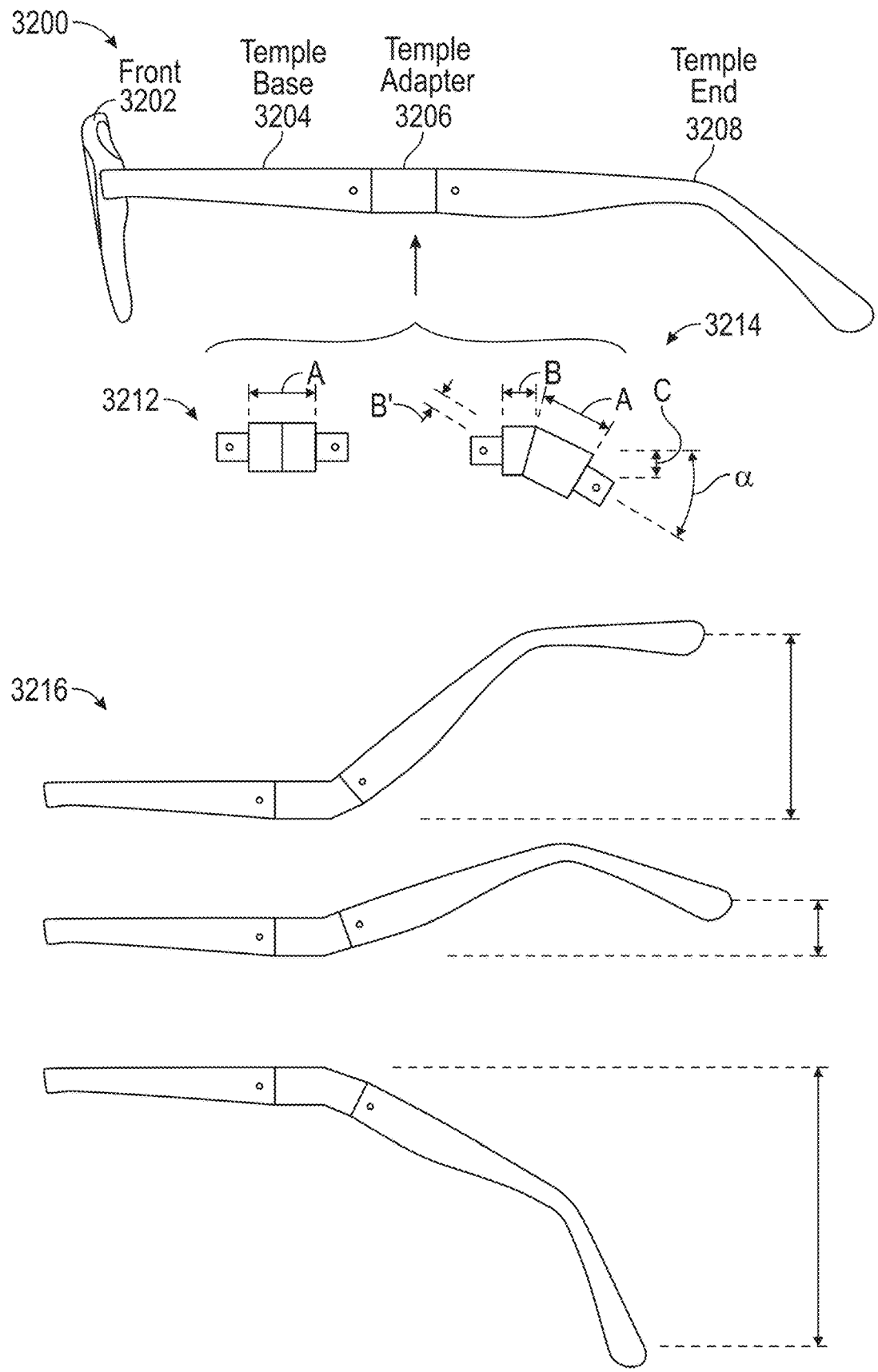
FIG. 32 illustrates a pair of eyeglasses assembled from multiple sections according to some embodiments of the disclosed technologies.

In some embodiments, the eyeglasses may be divided into multiple sections, and the eyeglass parameters may be used to select a combination of the sections. FIG. 32 illustrates a pair of eyeglasses 3200 assembled from multiple sections according to some embodiments of the disclosed technologies. Referring to FIG. 32, the sections of the eyeglasses 3200 may include a front 3202, a temple base 3204, a temple adapter 3206, and a temple end 3208. Each of the sections may come in different sizes, angles, and the like. For example, the temple adapter 3206 may be straight, as shown at 3212, or may have a specified angle, at 3214. Temple adapters 3206 having different angles may be selected to assemble eyeglasses having different positive and negative temple angles, as shown at 3216. It should be appreciated that the number and type of sections may differ from those shown in FIG. 32, may be selected to attain a desired number of stock keeping units.

Figure 33:
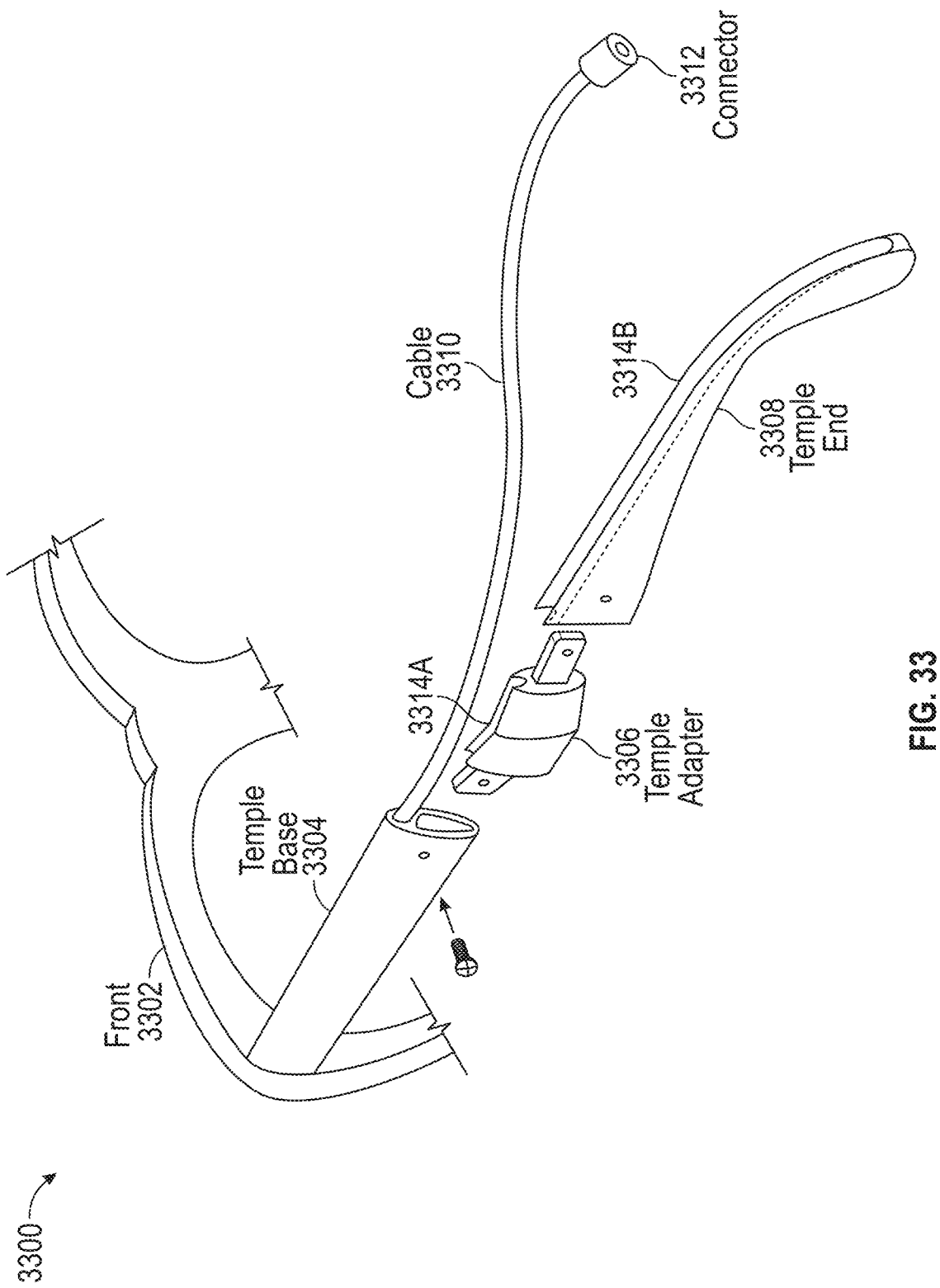
FIG. 33 illustrates a pair of display eyewear assembled from multiple sections according to some embodiments of the disclosed technologies.

In some embodiments, display eyewear may be divided into multiple sections in a similar manner, and the parameters may be used to select a combination of the sections. FIG. 33 illustrates a pair of display eyewear 3300 assembled from multiple sections according to some embodiments of the disclosed technologies. Referring to FIG. 33, the sections of the eyeglasses 3300 may include a front 3302, a temple base 3304, a temple adapter 3306, and a temple end 3308. Also shown is a cable 3310 having a magnetic breakaway connector 3312 and grooves 3314A,B for retaining the cable in the temple sections.

Each of the sections may come in different sizes, angles, and the like. For example, the temple adapter 3306 may be straight, as shown at 3312, or may have a specified angle, at 3314. Temple adapters 3306 having different angles may be selected to assemble eyeglasses having different positive and negative temple angles, as shown at 3316 to accommodate different right and left ear rest position heights in an effort to position the front of the frame or the centers of the displays optimally with regard to the centers of the right and left pupils. The temple adapters or temple sections having different angles are useful when unequal right and left ear rest heights or unequal right and left pupil center heights are presented and when the pantoscopic angles of the right and left sides of the frames are not adjustable.

Figure 34A:
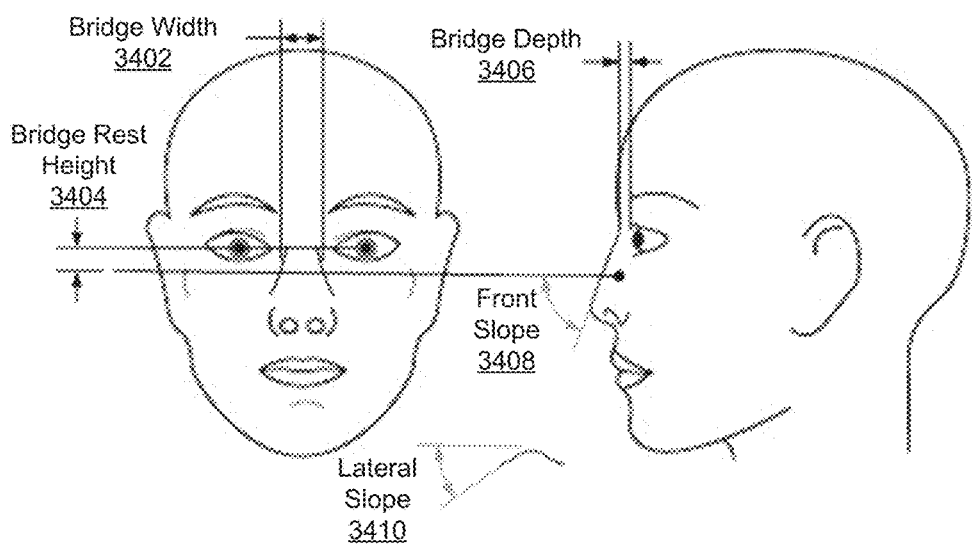
FIGS. 34A,B,C illustrate example nose shape metrics that may be determined from captured images of a user's head for selecting bridge inserts according to some embodiments of the disclosed technologies.
Figure 34B:
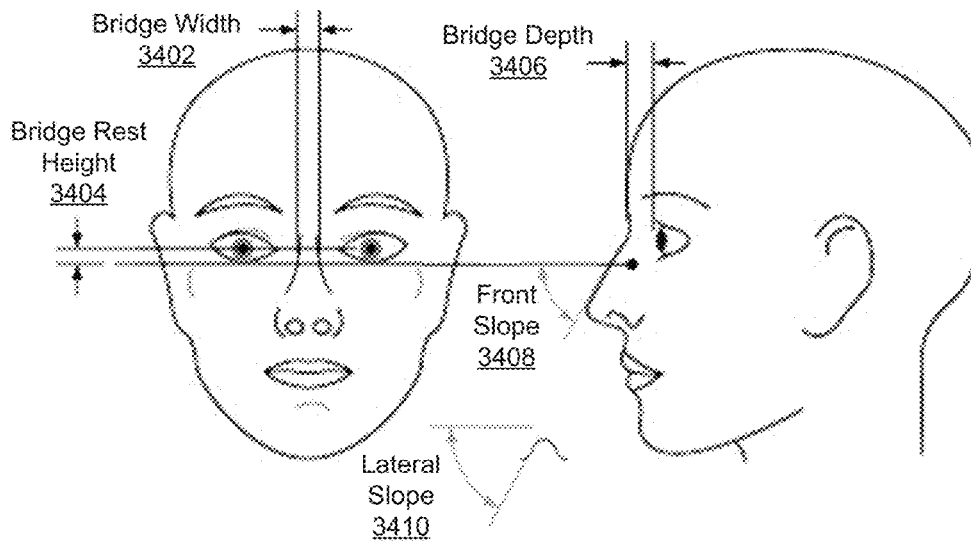
Figure 34C:
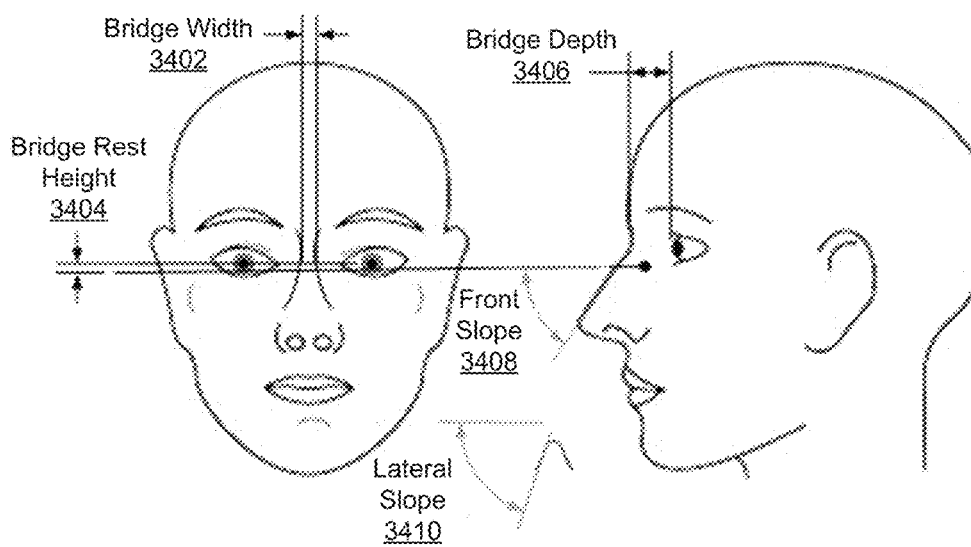

It should be appreciated that the number and type of sections may differ from those shown in FIG. 33, may be selected to attain a desired number of stock keeping units. For example, in some embodiments the sections may include a plurality of bridge inserts to accommodate different face and/or nose shapes. FIGS. 34A,B,C illustrate example face and nose shape metrics that may be determined from captured images of a user's head for selecting bridge inserts according to some embodiments of the disclosed technologies. The metrics include a bridge width 3402, a bridge rest height 3404, a bridge depth 3406, a front slope 3408, and a lateral slope 3410. It should be appreciated that other metrics may be used. FIGS. 34A,B,C depict these metrics for three different nose types. FIG. 34A illustrates a shallow, wide nose type. FIG. 34B illustrates a median nose type. FIG. 34C illustrates a deep, narrow nose type.

In some embodiments, these head and face metrics are processed to manufacture a frame with determined parameters or select a frame from a collection of pre-fabricated frames, or select frame sections to be used to assemble a unique frame. In some embodiments, this processing may include the use of artificial intelligence techniques. For example, a machine-learning model may be trained using obtained metrics and associated parameters for a large number of users, using supervised and/or unsupervised training techniques. The trained machine-learning model may be provided with a user's metrics as inputs, and may provide the parameters as outputs.

Figure 35A:
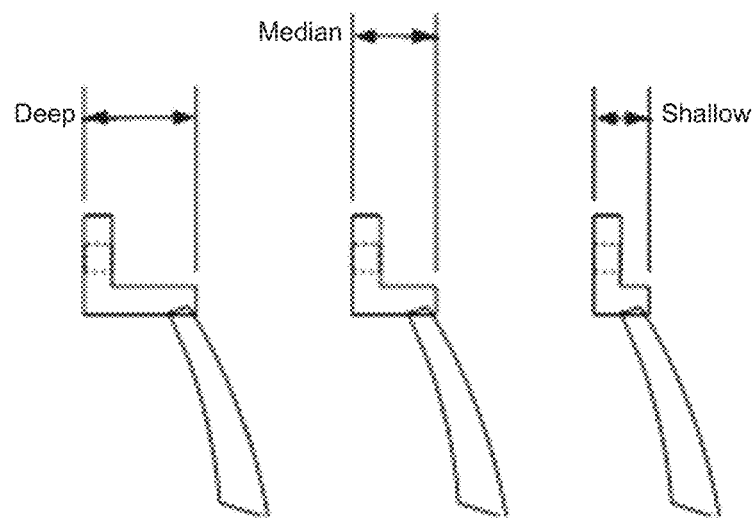
FIGS. 35A,B,C illustrate several different bridge inserts according to embodiments of the disclosed technologies.
Figure 35B:
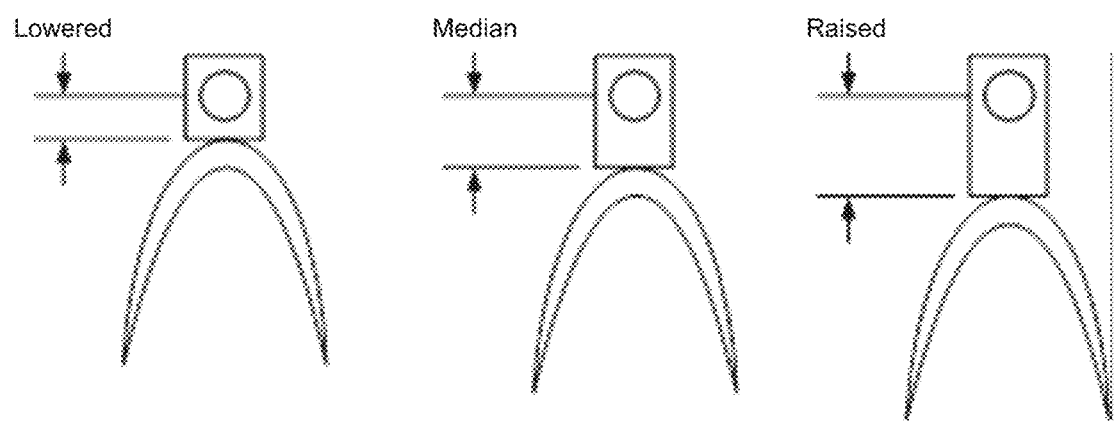
Figure 35C:
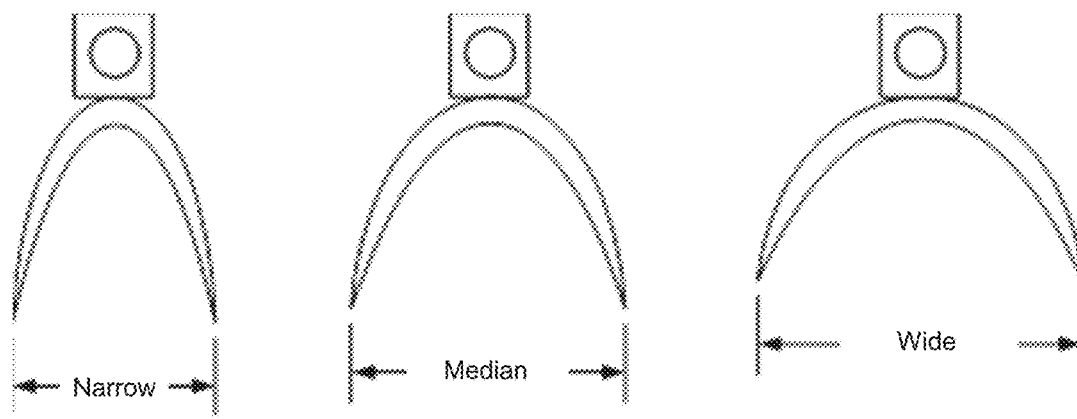

FIGS. 35A,B,C illustrate several different bridge inserts according to embodiments of the disclosed technologies. FIG. 35A is a side view of three bridge inserts that provide deep, median, and shallow vertex distances. FIG. 35B is a front view of three bridge inserts that are lowered, median, and raised. FIG. 35C is a front view of three bridge inserts that accommodate noses that are narrow, median, and wide.

Several embodiments of the disclosed technology have been described. It should be appreciated by those skilled in the relevant arts that these embodiments may be combined, and that features of one embodiment may be combined with features of one or more other embodiments.

Figure 36:
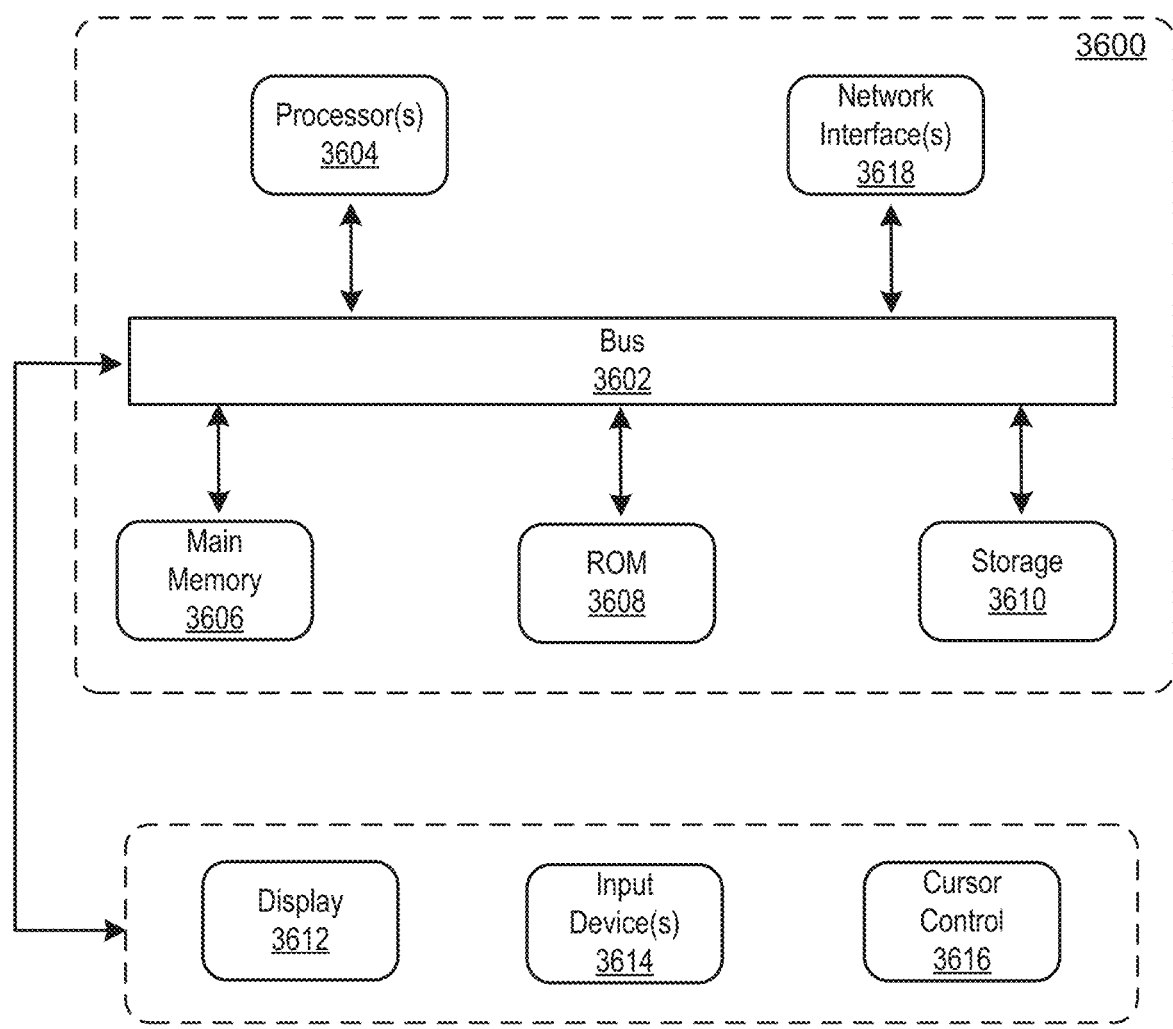
FIG. 36 depicts a block diagram of an example computer system in which embodiments described herein may be implemented.

FIG. 36 depicts a block diagram of an example computer system 3600 in which embodiments described herein may be implemented. The computer system 3600 includes a bus 3602 or other communication mechanism for communicating information, one or more hardware processors 3604 coupled with bus 3602 for processing information. Hardware processor(s) 3604 may be, for example, one or more general purpose microprocessors.

The computer system 3600 also includes a main memory 3606, such as a random access memory (RAM), cache and/or other dynamic storage devices, coupled to bus 3602 for storing information and instructions to be executed by processor 3604. Main memory 3606 also may be used for storing temporary variables or other intermediate information during execution of instructions to be executed by processor 3604. Such instructions, when stored in storage media accessible to processor 3604, render computer system 3600 into a special-purpose machine that is customized to perform the operations specified in the instructions.

The computer system 3600 further includes a read only memory (ROM) 3608 or other static storage device coupled to bus 3602 for storing static information and instructions for processor 3604. A storage device 3610, such as a magnetic disk, optical disk, or USB thumb drive (Flash drive), etc., is provided and coupled to bus 3602 for storing information and instructions.

The computer system 3600 may be coupled via bus 3602 to a display 3612, such as a liquid crystal display (LCD) (or touch screen), for displaying information to a computer user. An input device 3614, including alphanumeric and other keys, is coupled to bus 3602 for communicating information and command selections to processor 3604. Another type of user input device is cursor control 3616, such as a mouse, a trackball, or cursor direction keys for communicating direction information and command selections to processor 3604 and for controlling cursor movement on display 3612. In some embodiments, the same direction information and command selections as cursor control may be implemented via receiving touches on a touch screen without a cursor.

The computing system 3600 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 3600 may implement the techniques described herein using customized hard-wired logic, one or more ASICs or FPGAs, firmware and/or program logic which in combination with the computer system causes or programs computer system 3600 to be a special-purpose machine. According to one embodiment, the techniques herein are performed by computer system 3600 in response to processor(s) 3604 executing one or more sequences of one or more instructions contained in main memory 3606. Such instructions may be read into main memory 3606 from another storage medium, such as storage device 3610. Execution of the sequences of instructions contained in main memory 3606 causes processor(s) 3604 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 3610. Volatile media includes dynamic memory, such as main memory 3606. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 3602. Transmission media can also take the form of acoustic or light waves, such as those generated during radio-wave and infra-red data communications.

The computer system 3600 also includes a communication interface 3618 coupled to bus 3602. Network interface 3618 provides a two-way data communication coupling to one or more network links that are connected to one or more local networks. For example, communication interface 3618 may be an integrated services digital network (ISDN) card, cable modem, satellite modem, or a modem to provide a data communication connection to a corresponding type of telephone line. As another example, network interface 3618 may be a local area network (LAN) card to provide a data communication connection to a compatible LAN (or a WAN component to communicate with a WAN). Wireless links may also be implemented. In any such implementation, network interface 3618 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 3618, which carry the digital data to and from computer system 3600, are example forms of transmission media.

The computer system 3600 can send messages and receive data, including program code, through the network (s), network link and communication interface 3618. In the Internet example, a server might transmit a requested code for an application program through the Internet, the ISP, the local network and the communication interface 3618.

The received code may be executed by processor 3604 as it is received, and/or stored in storage device 3610, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, or a combination of hardware and software. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 3600.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. A method comprising:
   disposing a physical landmark upon an eye of a user;
   capturing at least one image of the eye of the user with an image sensor while the eye is illuminated, wherein the image includes an image of the physical landmark and at least one other point on the surface of the eye outside of the cornea;
   processing the at least one image to obtain at least one metric of the eye of the user;
   determining, based on the at least one metric, at least one parameter of a daily use contact lens to be worn on the eye of the user;
   disposing measurement display eyewear on the face of the user prior to capturing the image, the measurement display eyewear comprising a display, the light source, and the image sensor; and
   capturing the at least one image of the eye of the user and the physical landmark with the display eyewear while the eye is illuminated;
   wherein the obtained at least one metric further comprises at least one of:
      a vertex distance between an apex of a cornea of the eye and the display,
      a pupillary distance between the center of a pupil of an eye and the midline of the face between the eyes, or
      a vertical position of the center of the pupil relative to the center of the display.

2. The method of claim 1, wherein:
   the daily use contact lens is to be worn by the user to view daily use display eyewear.

3. The method of claim 1, wherein:
   the physical landmark is a measurement contact lens.

4. The method of claim 3, wherein:
   the measurement contact lens comprises an orientation mark; and
   capturing at least one image of the eye of the user and the physical landmark with an image sensor while the eye is illuminated comprises capturing at least one image of the orientation mark.

5. The method of claim 1, wherein:
   the physical landmark comprises a liquid film.

6. The method of claim 5, wherein:
   the liquid film reflects light in the spectrum of the image sensor.

7. The method of claim 1, further comprising:
   disposing a measurement contact lens upon the eye of the user prior to capturing the at least one image, wherein the measurement contact lens conforms to the shape of the eye of the user and at least one point on the measurement contact lens is detectable by the image sensor.

8. A non-transitory machine-readable storage medium encoded with instructions executable by one or more hardware processors of a computing component, the machine-readable storage medium comprising instructions to cause the one or more hardware processors to perform operations comprising:
   receiving at least one image of an eye of a user captured while a physical landmark is on the eye and the eye is illuminated, wherein the image includes an image of the physical landmark and at least one other point on the surface of the eye outside of the cornea;
   processing the at least one image to obtain at least one metric of the eye of the user; and
   determining, based on the at least one metric, at least one parameter of a daily use contact lens to be worn on the eye of the user;
   wherein the at least one image is captured by measurement display eyewear worn on the face of the user; and
   wherein the obtained at least one metric further comprises at least one of:
      a vertex distance between an apex of a cornea of the eye and a display of the measurement display eyewear;
      a pupillary distance between the center of a pupil of an eye and the midline of the face between the eyes; or
      a vertical position of the center of the pupil relative to the center of the display.

9. The non-transitory machine-readable storage medium of claim 8, wherein:
   the daily use contact lens is to be worn by the user to view daily use display eyewear.

10. The non-transitory machine-readable storage medium of claim 8, wherein:
   the physical landmark is a measurement contact lens.

11. The non-transitory machine-readable storage medium of claim 10, wherein:

the measurement contact lens comprises an orientation mark; and the at least one image includes an image of the orientation mark.

12. The non-transitory machine-readable storage medium of claim 10, wherein:

the measurement contact lens conforms to the surface of the eye; and at least one point on the measurement contact lens is detectable by an image sensor that generated the image.

13. The non-transitory machine-readable storage medium of claim 8, wherein:

the physical landmark comprises a liquid film.

14. The non-transitory machine-readable storage medium of claim 13, wherein:

the liquid film reflects light in the spectrum of the image sensor that generated the image.

15. A system, comprising:

a hardware processor; and a non-transitory machine-readable storage medium encoded with instructions executable by the hardware processor to perform operations comprising:

receiving at least one image of an eye of a user captured while a physical landmark is on the eye and the eye is illuminated, wherein the image includes an image of the physical landmark and at least one other point on the surface of the eye outside of the cornea;

processing the at least one image to obtain at least one metric of the eye of the user; and determining, based on the at least one metric, at least one parameter of a daily use contact lens to be worn on the eye of the user;

wherein the at least one image is captured by measurement display eyewear worn on the face of the user; and wherein the obtained at least one metric further comprises at least one of:

a vertex distance between an apex of a cornea of the eye and a display of the measurement display eyewear;

a pupillary distance between the center of a pupil of an eye and the midline of the face between the eyes; or a vertical position of the center of the pupil relative to the center of the display.

16. The system of claim 15, wherein:

the daily use contact lens is to be worn by the user to view daily use display eyewear.

17. The system of claim 15, wherein:

the physical landmark is a measurement contact lens.

18. The system of claim 17, wherein:

the measurement contact lens comprises an orientation mark; and the at least one image includes an image of the orientation mark.

19. The system of claim 17, wherein:

the measurement contact lens conforms to the surface of the eye; and at least one point on the measurement contact lens is detectable by an image sensor that generated the image.

20. The system of claim 15, wherein:

the physical landmark comprises a liquid film.

21. The system of claim 20, wherein:

the liquid film reflects light in the spectrum of the image sensor that generated the image.

\* \* \* \* \*